United States Patent
Anderson et al.

(10) Patent No.: US 9,907,746 B2
(45) Date of Patent: Mar. 6, 2018

(54) METHODS FOR PREPARING VESICLES AND FORMULATIONS PRODUCED THEREFROM

(75) Inventors: David E. Anderson, Boston, MA (US); Francisco Diaz-Mitoma, Ottawa (CA); Hoang-Thanh Le, Ottawa (CA)

(73) Assignee: Variation Biotechnologies, Inc., Ottawa (CA)

( * ) Notice: Subject to any disclaimer, the term of this patent is extended or adjusted under 35 U.S.C. 154(b) by 104 days.

(21) Appl. No.: 13/377,371

(22) PCT Filed: Jul. 6, 2010

(86) PCT No.: PCT/US2010/041081
§ 371 (c)(1),
(2), (4) Date: Apr. 2, 2012

(87) PCT Pub. No.: WO2011/005772
PCT Pub. Date: Jan. 13, 2011

(65) Prior Publication Data
US 2012/0177683 A1    Jul. 12, 2012

Related U.S. Application Data

(60) Provisional application No. 61/223,192, filed on Jul. 6, 2009, provisional application No. 61/256,909, filed on Oct. 30, 2009.

(51) Int. Cl.
*A61K 9/127*   (2006.01)
*A61K 39/12*   (2006.01)
*A61K 9/00*    (2006.01)
*A61K 39/00*   (2006.01)

(52) U.S. Cl.
CPC ............ *A61K 9/0019* (2013.01); *A61K 9/127* (2013.01); *A61K 9/1277* (2013.01); *A61K 39/12* (2013.01); *A61K 2039/5252* (2013.01); *A61K 2039/5254* (2013.01); *A61K 2039/55555* (2013.01); *C12N 2770/24234* (2013.01)

(58) Field of Classification Search
None
See application file for complete search history.

(56) References Cited

U.S. PATENT DOCUMENTS

| | | |
|---|---|---|
| 3,952,097 A | 4/1976 | Levy |
| 4,024,241 A | 5/1977 | Levy |
| 4,349,538 A | 9/1982 | Levy |
| 4,352,884 A | 10/1982 | Nakashima et al. |
| 4,436,727 A | 3/1984 | Ribi |
| 4,537,769 A | 8/1985 | Cerini |
| 4,866,034 A | 9/1989 | Ribi |
| 4,877,611 A | 10/1989 | Cantrell |
| 4,894,228 A | 1/1990 | Purcell et al. |
| 4,912,094 A | 3/1990 | Myers et al. |
| 4,983,387 A | 1/1991 | Goldstein et al. |
| 5,057,540 A | 10/1991 | Kensil et al. |
| 5,160,669 A | 11/1992 | Wallach et al. |
| 5,250,236 A | 10/1993 | Gasco |
| 5,340,588 A | 8/1994 | Domb |
| 5,393,527 A | 2/1995 | Malick et al. |
| 5,549,910 A | 8/1996 | Szoka, Jr. |
| 5,567,434 A | 10/1996 | Szoka, Jr. |
| 5,653,996 A | 8/1997 | Hsu |
| 5,679,355 A | 10/1997 | Alexander et al. |
| 5,817,318 A | 10/1998 | Sia et al. |
| 5,853,753 A * | 12/1998 | Maierhofer et al. .......... 424/450 |
| 5,858,368 A | 1/1999 | Smith et al. |
| 5,861,243 A | 1/1999 | Dietrich et al. |
| 5,876,721 A | 3/1999 | Alexander et al. |
| 5,879,703 A | 3/1999 | Fountain |
| 5,910,306 A | 6/1999 | Alving et al. |
| 5,919,480 A | 7/1999 | Kedar et al. |
| 5,948,410 A | 9/1999 | Van Scharrenburg et al. |
| 5,962,298 A | 10/1999 | Fiers et al. |
| 5,977,081 A | 11/1999 | Marciani |
| 6,005,099 A | 12/1999 | Davies et al. |

(Continued)

FOREIGN PATENT DOCUMENTS

| CA | 2258907 A1 | 12/1997 |
|---|---|---|
| CN | 1169161 A | 12/1997 |

(Continued)

OTHER PUBLICATIONS

Lasic, Novel applications of liposomes, 1998, Tibtech, vol. 16. pp. 307-321.*
Vangala et al., A comparative study of cationic liposome and niosome-based adjuvant systems for protein subunit vaccines: characterisation, environmental scanning electron microscopy and immunisation studies in mice, 2006, Journal of Pharmacy and Pharmacology, vol. 58, pp. 787-799.*
Khmelnitsky et al., Denaturation capacity: a new quantitative criterion for selection of organic solvents as reaction media in biocatalysis, 1991, European Journal of Biochem., vol. 198, pp. 31-41.*
Oku et al., Effect of serum protein binding on real-time trafficking of liposomes with different charges analyzed by positron emission tomography, 1996, Biochimica et Biophysica Acta, vol. 1280, pp. 149-154.*
Alexopoulou et al., "Preparation and characterization of lyophilized liposomes with incorporated quercetin," J Liposome Res. 16(1): 17-25, 2006.

(Continued)

*Primary Examiner* — Benjamin P Blumel
(74) *Attorney, Agent, or Firm* — Choate, Hall & Stewart LLP; Charles E. Lyon; Rolando Medina (57) ABSTRACT

The present disclosure provides methods for preparing vesicles. In general, these methods include steps of providing a lyophilized lipid product and rehydrating the lyophilized lipid product with an aqueous solution comprising an antigen such that antigen-containing vesicles are formed. The lyophilized lipid product is prepared by dissolving vesicle-forming lipids in a polar-protic water-miscible organic solvent to produce a lipid solution and then lyophilizing the lipid solution. The present disclosure also provides antigen-containing vesicle formulations prepared using these methods. The present disclosure also provides kits that include a lyophilized lipid product in a first container and an aqueous solution comprising an antigen in a second container.

9 Claims, 2 Drawing Sheets

(56) References Cited

U.S. PATENT DOCUMENTS

| | | |
|---|---|---|
| 6,080,725 A | 6/2000 | Marciani |
| 6,090,392 A | 7/2000 | Berman |
| 6,136,606 A | 10/2000 | Chatfield |
| 6,180,110 B1 | 1/2001 | Funkhouser et al. |
| 6,207,178 B1 | 3/2001 | Westesen et al. |
| 6,235,888 B1 | 5/2001 | Pachuk et al. |
| 6,248,363 B1 | 6/2001 | Patel et al. |
| 6,287,570 B1 | 9/2001 | Foley |
| 6,290,967 B1 | 9/2001 | Volkin et al. |
| 6,303,347 B1 | 10/2001 | Johnson et al. |
| 6,344,354 B1 | 2/2002 | Webster et al. |
| 6,372,223 B1 | 4/2002 | Kistner et al. |
| 6,383,806 B1 | 5/2002 | Rios |
| 6,500,623 B1 | 12/2002 | Tung |
| 6,503,753 B1 | 1/2003 | Rios |
| 6,534,065 B1 | 3/2003 | Makin et al. |
| 6,538,123 B2 | 3/2003 | Barban |
| 6,541,003 B1 | 4/2003 | Smith |
| 6,605,457 B1 | 8/2003 | Fiers et al. |
| 6,635,246 B1 | 10/2003 | Barrett et al. |
| 6,649,410 B2 | 11/2003 | Rios |
| 6,653,130 B2 | 11/2003 | Rios |
| 6,692,955 B1 | 2/2004 | Meredith et al. |
| 6,706,859 B1 | 3/2004 | Sörensen |
| 6,740,325 B1 | 5/2004 | Arnon et al. |
| 6,743,900 B2 | 6/2004 | Burt et al. |
| 6,764,840 B2 | 7/2004 | Johnson et al. |
| 6,787,351 B2 | 9/2004 | Chen et al. |
| 6,831,169 B2 | 12/2004 | Pachuk et al. |
| 6,861,244 B2 | 3/2005 | Barrett et al. |
| 6,991,929 B1 | 1/2006 | D'hondt |
| 7,052,701 B2 | 5/2006 | Barrett et al. |
| 7,063,849 B1 | 6/2006 | Thibodeau et al. |
| 7,067,134 B1 | 6/2006 | Kang et al. |
| 7,192,595 B2 | 3/2007 | Arnon et al. |
| 7,244,435 B2 | 7/2007 | Lai |
| 7,262,045 B2 | 8/2007 | Schwartz et al. |
| 7,316,813 B2 | 1/2008 | Eichhorn |
| 7,348,011 B2 | 3/2008 | Guntaka et al. |
| 7,361,352 B2 | 4/2008 | Birkett et al. |
| 7,399,840 B2 | 7/2008 | Burt et al. |
| 7,468,259 B2 | 12/2008 | Fiers et al. |
| 7,494,659 B2 | 2/2009 | Katinger et al. |
| 7,510,719 B2 | 3/2009 | Dang et al. |
| 7,514,086 B2 | 4/2009 | Arnon et al. |
| 7,527,800 B2 | 5/2009 | Yang et al. |
| 7,537,768 B2 | 5/2009 | Luke et al. |
| 9,610,248 B2 | 4/2017 | Anderson et al. |
| 2002/0164648 A1 | 11/2002 | Goins et al. |
| 2003/0092145 A1 | 5/2003 | Jira et al. |
| 2004/0022840 A1 | 2/2004 | Nagy et al. |
| 2004/0081688 A1 | 4/2004 | Del Curto et al. |
| 2005/0042230 A1 | 2/2005 | Anderson et al. |
| 2005/0095283 A1 | 5/2005 | Castor et al. |
| 2005/0169979 A1* | 8/2005 | Michaeli et al. ............ 424/450 |
| 2005/0214331 A1 | 9/2005 | Levy |
| 2006/0121105 A1 | 6/2006 | Barenholz et al. |
| 2006/0257852 A1 | 11/2006 | Rappuoli et al. |
| 2007/0142315 A1 | 6/2007 | Forsbach et al. |
| 2007/0224257 A1 | 9/2007 | Commander et al. |
| 2007/0264273 A1 | 11/2007 | Barenholz et al. |
| 2008/0057080 A1 | 3/2008 | Luke et al. |
| 2008/0131466 A1 | 6/2008 | Reed et al. |
| 2008/0145375 A1 | 6/2008 | Bembridge et al. |
| 2008/0160089 A1 | 7/2008 | Vitiello et al. |
| 2008/0181914 A1 | 7/2008 | Eichhorn |
| 2008/0213461 A1 | 9/2008 | Gill et al. |
| 2008/0268028 A1 | 10/2008 | Zurbriggen et al. |
| 2008/0286353 A1 | 11/2008 | Gregoriadis |
| 2009/0028903 A1 | 1/2009 | Hanon et al. |
| 2009/0041809 A1 | 2/2009 | Emtage |
| 2009/0081157 A1 | 3/2009 | Kornbluth et al. |
| 2009/0081254 A1 | 3/2009 | Vajdy et al. |
| 2009/0117141 A1 | 5/2009 | Torres et al. |
| 2009/0155309 A1 | 6/2009 | Friede et al. |
| 2009/0181078 A1 | 7/2009 | Reed et al. |
| 2009/0202620 A1 | 8/2009 | Turnell et al. |
| 2010/0062071 A1 | 3/2010 | Loxley et al. |
| 2010/0080844 A1 | 4/2010 | Bacon et al. |
| 2010/0129392 A1 | 5/2010 | Shi et al. |
| 2010/0226932 A1 | 9/2010 | Smith et al. |
| 2011/0177163 A1 | 7/2011 | Diaz-Mitoma et al. |
| 2012/0156240 A1 | 6/2012 | Anderson et al. |
| 2012/0276125 A1 | 11/2012 | Ast et al. |
| 2013/0108692 A1 | 5/2013 | Anderson et al. |
| 2013/0295165 A1 | 11/2013 | Anderson et al. |
| 2013/0323280 A1 | 12/2013 | Anderson et al. |
| 2014/0356399 A1 | 12/2014 | Anderson |
| 2015/0079077 A1 | 3/2015 | Kirchmeier et al. |

FOREIGN PATENT DOCUMENTS

| | | |
|---|---|---|
| CN | 101574394 A | 11/2009 |
| EP | 0413637 A1 | 2/1991 |
| EP | 0 433242 A1 | 6/1991 |
| EP | 0489153 A1 | 6/1992 |
| EP | 729473 B1 | 8/2000 |
| EP | 1 129 723 A1 | 9/2001 |
| EP | 2014279 A1 | 1/2009 |
| GB | 2122204 | 1/1984 |
| WO | WO-88/06882 A1 | 9/1988 |
| WO | WO9002965 | 3/1990 |
| WO | WO-92/00081 A1 | 1/1992 |
| WO | WO-93/19781 A1 | 10/1993 |
| WO | WO-95/09651 A1 | 4/1995 |
| WO | WO-95/14026 A1 | 5/1995 |
| WO | WO9517210 | 6/1995 |
| WO | WO-96/11280 A1 | 4/1996 |
| WO | WO-97/04768 A1 | 2/1997 |
| WO | WO9801139 | 1/1998 |
| WO | WO-98/50399 A1 | 11/1998 |
| WO | WO-99/62500 A1 | 12/1999 |
| WO | WO-01/05374 A1 | 1/2001 |
| WO | WO-02/051390 A2 | 7/2002 |
| WO | WO-03/011223 A2 | 2/2003 |
| WO | WO-03/099195 A2 | 12/2003 |
| WO | WO-2005/117958 A1 | 12/2005 |
| WO | WO-2007/110776 A1 | 10/2007 |
| WO | WO-2008/153236 A1 | 12/2008 |
| WO | WO-2009/029695 A1 | 3/2009 |
| WO | WO-2009/091531 A2 | 7/2009 |
| WO | WO-2009/155489 A2 | 12/2009 |
| WO | WO-2010033812 A1 | 3/2010 |
| WO | WO-2011/005769 A1 | 1/2011 |
| WO | WO-2011/005772 A1 | 1/2011 |
| WO | WO-2012/006368 A2 | 1/2012 |
| WO | WO-2012/097347 A1 | 7/2012 |

OTHER PUBLICATIONS

Alpan et al., "The role of dentritic cells, B cells, and M cells in gut-oriented immune responses," J Immunol 166(8): 4843-4852, 2001.

Andre et al., "Inactivated candidate vaccines for hepatitis A," Prog Med Virol. 37: 72-95, 1990.

Bangham et al., "Diffusion of univalent ions across the lamellae of swollen phospholipids," J. Mol. Biol. 13(1): 238-252, 1965.

Cregg et al., "High-Level Expression and Efficient Assembly of Hepatitis B Surface Antigen in the Methylotrophic Yeast, Pichia Pastoris," Biotechnology 5: 479-485, 1987.

Fattovich G., "Natural history of hepatitis B," J Hepatol. 39 Suppl 1: S50-S58, 2003.

Field et al., "Inducers of interferon and host resistance. II. Multistranded synthetic polynucleotide complexes," Proc Natl Acad Sci USA 58(3): 1004-1010, 1967.

Harford et al., "Expression of hepatitis B surface antigen in yeast," Dev Biol Stand. 54: 125-130, 1983.

Hilleman MR., "Critical overview and outlook: pathogenesis, prevention, and treatment of hepatitis and hepatocarcinoma caused by hepatitis B virus," Vaccine 21(32): 4626-4649, 2003.

International Search Report for PCT/US10/41078, dated Aug. 23, 2010.

(56) References Cited

OTHER PUBLICATIONS

Kasraian and DeLuca, "Thermal Analysis of the Tertiary Butyl Alcohol-Water System and Its Implications on Freeze-Drying," Pharm. Res., 12(4): 484-490, 1995.
Kasraian and DeLuca, "The Effect of Tertiary Butyl Alcohol on the Resistance of the Dry Product Layer During Primary Drying," Pharm. Res., 12(4): 491-495, 1995.
Levy et al., "Inhibition of tumor growth by polyinosinic-polycytidylic acid," Proc Natl Acad Sci USA 62(2): 357-361, 1969.
Li and Deng, "A novel method for the preparation of liposomes: freeze drying of monophase solutions," J Pharm Sci 93(6): 1403-1414, 2004.
Mao et al., "Further evaluation of the safety and protective efficacy of live attenuated hepatitis A vaccine (H2-strain) in humans," Vaccine 15(9): 944-947, 1997.
McAleer et al., "Human hepatitis B vaccine from recombinant yeast," Nature 307(5947): 178-180, 1984.
Miller et al., "Hepatitis C virus shares amino acid sequence similarity with pestiviruses and flaviviruses as well as members of two plant virus supergroups," Proc. Natl. Acad. Sci. 87: 2057-2061, 1990.
Mowat AM, "Dentritic cells and immune responses to orally administered antigens," Vaccine 23(15): 1797-1799, 2005.
Provost et al., "New findings in live, attenuated hepatitis A vaccine development," J Med Virol. 20(2): 165-175, 1986.
Valenzuela et al., "Chemical synthesis of a gene for human epidermal growth factor urogastrone and its expression in yeast," Proc Natl. Acad Sci USA 80(24): 7461-7465, 1983.
Walde and Ichikawa, "Enzymes inside lipid vesicles: preparation, reactivity and applications," Biomol Eng. 18(4): 143-177, 2001.
Weiner et al., "Variable and hypervariable domains are found in the regions of HCV corresponding to the flavivirus envelope and NS1 proteins and the pestivirus envelope glycoproteins," Virology 180(2): 842-848, 1991.
Written Opinion for PCT/US10/41078, dated Aug. 23, 2010.
International Search Report for PCT/US10/41081 dated Oct. 26, 2010.
Written Opinion for PCT/US10/41081 dated Oct. 26, 2010.
Yan et al., "Recent Advances in Liposome-Based Nanoparticles for Antigen Delivery." Polymer Reviews [online], vol. 47, Iss. 3, pp. 329-344, 2007.
Collins et al., Non-Ionic Surfactant Vesicle Formulation of Stibogluconate for Canine Leishmaniasis, Journal of Pharmacy and Pharmacology, 42(S1):53F (1990).
International Preliminary Report on Patentability for PCT/US2010/041078, dated Jan. 19, 2012 (12 pages).
International Preliminary Report on Patentability for PCT/US2010/041081, dated Jan. 19, 2012 (9 pages).
Kirby et al., Dehydration-Rehydration Vesicles: A Simple Method for High Yield Drug Entrapment in Liposomes, Nature Biotechnology, 2(11):979-984 (1984).
Mann et al., Optimisation of a Lipid Based Oral Delivery System Containing A/Panama Influenza Haemagglutinin, Vaccine, 22:2425-2429 (2004).
Pick, Liposomes With a Large Trapping Capacity Prepared by Freezing and Thawing of Sonicated Phospholipid Mixtures, Arch. Biochem. Biophys, 212(1):186-194 (1981).
Varun et al., Niosomes and Liposomes—Vesicular Approach Towards Transdermal Drug Delivery, International Journal of Pharmaceutical and Chemical Sciences, 1(3):632-644 (2012).
Chen et al., Research advances on Solid lipid nanoparticles as new drug carrier, Chinese Journal of Ethnomedicine and Ethnopharmacy, Issue 2, pp. 7-10, (2009).
Chen et al., An overview of liposome lyophilization and its future potential, Journal of Controlled Release, 142: 299-311 (2010).
Hassan, Y. et al., Immune responses in mice induced by HSV-1 glycoproteins presented with ISCOMs or NISV delivery systems, Vaccine, 14(17-18): 1581-9 (1996).
Huckriede, A. et al., The virosome concept for influenza vaccines, Vaccine, 23(Suppl 1): S26-38 (2005).
Jurk, et al., Modulating Responsiveness of Human TLR7 and 8 to Small Molecule Ligands With T-rich Phosphorothiate Oligodeoxynucleotides, Eur. J. Immunol., 36(7) :1815-26 (2006).
Lavanchy, The Importance of Global Surveillance of Influenza, Vaccine, 17: S24-S25 (1999).
Russell, DG and Alexander, J., Effective immunization against cutaneous leishmaniasis with defined membrane antigens reconstituted into liposomes, Journal of Immunology, 140(4):1274-1279 (1988).
Salager, J-L., Surfactants—Types and Uses, FIRP Booklet #E300-A, Teaching Aid in Surfactant Science & Engineering, in English, Laboratory of Formulation, Interfaces, Rheology and Processes, Universidad de Los Andes, Version 2: 1-50 (2002).
Schalk, JA et al., Estimation of the number of infectious measles viruses in live virus vaccines using quantitative real-time PCR, Journal of Virological Methods, 117(2): 179-187 (2004).
Schubert et al., Solvent Injection as a New Approach for Manufacturing Lipid Nanoparticles—Evaluation of the Method and Process Parameters, European Journal of Pharmaceuticals and Biopharmaceutics, 55: 125-131 (2003).
Szoka, Jr., F. and Papahadjopoulos, D., Comparative Properties and Methods of Preparation of Lipid Vesicles (Liposomes)1, Ann. Rev. Viophys. Bioeng., 9: 467-508 (1980).
Uchegbu, I.F. And Vyas, S.P., Non-ionic surfactant based vesicles (niosomes) in drug delivery, in International Journal of Pharmaceuticals, 172: 33-70 (1998).
Verma, S. et al., Nanoparticle vesicular systems: A versatile tool for drug delivery, Journal of Chemical and Pharmaceutical Research, 2(2): 496-509 (2010).
Wagner et al., Liposome Technology for Industrial Purposes, J. Drug Delivery, vol. 2011, Article ID 591325 (9 pages) (2010).
Wang et al., Solvent Injection-Lyophilization of Tert-Butyl Alcohol/Water Cosolvent Systems for the Preparation of Drug-Loaded Solid Lipid Nanoparticles, Colloids and Surfaces B: Biointerfaces, 79: 254-261 (2010).
World Health Organization, The Immunological Basis for Immunization Series, Model 7: Measles (2009).
Mozafari, M.R., Nanomaterials and Nanosystems for Biomedical Applications, Springer, 1-159 (2007).
Hofland, H.E.J. et al., Nonionic Surfactant Vesicles: A Study of Vesicle Formation, Characterization and Stability, Journal of Colloid and Interface Science, 161(2): 366-376, Abstract Only, 2 pages (1993).
Kumar, G.P. et al., Nonionic surfactant vesicular systems for effective drug delivery—an overview, Acta Pharmaceutica Sinica B, 1(4): 208-219 (2011).
Tarekegn, A. et al., Niosomes in Targeted Drug Delivery: Some Recent Advances, International Journal of Pharmaceutical Sciences and Research, 1(9): 1-8 (2010).
International Search Report for PCT/US09/57492, 2 pages (Nov. 20, 2009).
Mann et al., Optimisation of a Lipid Based Oral Delivery System Containing A/Panama Influenza Haemagglutinin, Vaccine, 22: 2425-2429 (2004).
Written Opinion for PCT/US09/57492, 5 pages (Nov. 20, 2009).
Bramwell, V. et al., Particulate delivery systems for vaccines: what can we expect?, The Journal of Pharmacy and Pharmacology, 58(6): 717-728 (2006).
Conacher, M. et al., Oral immunisation with peptide and protein antigens by formulation in lipid vesicles incorporating bile salts (bilosomes), Vaccine, 19(20-22): 2965-2974 (2001).
Gnjatic, S. et al., TLR Agonists, The Cancer Journal, 16(4): 382-391 (2010).
Manosroi, A. et al., Characterization of vesicles prepared with various non-ionic surfactants mixed with cholesterol, Colloids and Surfaces B: Biointerfaces, 30(1-2): 129-138 (2003).
Van Hal, D. A. et al., Preparation and Characterization of Nonionic Surfactant Vesicles, Journal of Colloid and Interface Science, 178(1): 263-273 (1996).
Anderson, R.J., Properties of Cholesterol Obtained from Different Sources, J. Biol. Chem., 71: 4007-418 (1927).
CAS Registry 18656-38-7, Record for Dimyristoyl phosphatidylcholine, 2 pages (Nov. 16, 1984).

(56) References Cited

OTHER PUBLICATIONS

Israelachvili, J.N. et al., Physical Principles of Membrane Organization, Quarterly Reviews of Biophysics, 13(2): 121-200 (1980).
Jiang et al., Advances in non-ionic surfactant based vesicles, Chinese Journal of Modern Drug Application, 1:(11): 98-101 (2007). English Translation, pp. 1-8.
Senior, J. and Radomsky, M., Liposomes for Local Sustained Drug Release, Sustained-Release Injectable Products, Chapter 7: 137-180 (Published Sep. 30, 2005).
Bennett, E. et al., Translational modifications to improve vaccine efficacy in an oral influenza vaccine, methods, 49: 322-327 (2009).

\* cited by examiner

METHODS FOR PREPARING VESICLES AND FORMULATIONS PRODUCED THEREFROM

CROSS REFERENCE TO RELATED APPLICATIONS

The present application is the National Stage of International Application No. PCT/US2010/041081, filed Jul. 6, 2010, which claims priority under 35 U.S.C. § 119(e) to U.S. provisional application Ser. No. 61/223,192, filed Jul. 6, 2009 and U.S. provisional application Ser. No. 61/256,909, filed Oct. 30, 2009, the entire contents of each of which are hereby incorporated by reference.

BACKGROUND

Vesicles were first described in the 1960s as a model of cellular membranes (see Bangham et al., *J. Mol. Biol.* 13:238-252, 1965). Vesicles have found a number of applications in the delivery of small molecule drugs, vaccine adjuvancy, gene transfer and diagnostic imaging (e.g., see *Liposome Technology*, 3$^{rd}$ Edition, Edited by Gregory Gregoriadis, Informa HealthCare, 2006 and *Liposomes: A Practical Approach* (*The Practical Approach Series*, 264), 2$^{nd}$ Edition, Edited by Vladimir Torchilin and Volkmar Weissig, Oxford University Press, USA, 2003).

A number of methods for preparing vesicles have been described (e.g., see references cited above and Walde and Ichikawa, *Biomol. Eng.*, 18:143-177, 2001). However, there remains a need in the art for methods that can be used to entrap substances within vesicles. One method for entrapping small molecules was originally described in 1995 which employed a tert-butanol and water co-solvent system (see Kasrian and DeLuca, *Pharm. Res.*, 12:484-490, 1995 and Kasrian and DeLuca, *Pharm. Res.*, 12:491-495, 1995). Specifically, the method involves dissolving the lipids (and any other organic solvent soluble materials) in tert-butanol and dissolving any water-soluble materials such as sucrose in water. These two solutions are then mixed in an appropriate ratio to produce a third monophase solution. The resulting solution is freeze-dried to form a lyophilized product. The lyophilized product is then reconstituted by the addition of an equal volume of water and gentle shaking, which leads to the formation of an aqueous suspension of vesicles. This method of vesicle preparation has been used to entrap small molecule drugs (e.g., see Li and Deng, *J. Pharm. Sci.* 93:1403-1414, 2004 and Alexopoulou et al., *J. Liposome Res.* 16:17-25, 2006). As described by Li and Deng, this has been achieved by either including the small molecule drug in the initial monophase solution (passive loading) or using pH gradients to load the small molecule drug into empty pre-formed vesicles (active loading).

While these methods may well be suitable for entrapping substances that can withstand contact with organic solvents such as tert-butanol and/or small molecules that are able to diffuse rapidly into empty vesicles we have found it unsuitable for entrapping the types of antigens (e.g., polypeptides, viruses, etc.) that are commonly involved in vaccines. In particular, we have found that these methods produce low entrapment efficiencies and can dramatically reduce the activity of the underlying antigen (e.g., as measured by immune responses). There is therefore a need in the art for methods of preparing vesicles that are capable of entrapping antigens while minimizing impact on antigen activity.

SUMMARY

In one aspect, the present disclosure provides methods for preparing vesicles. In general, these methods include steps of providing a lyophilized lipid product and rehydrating the lyophilized lipid product with an aqueous solution comprising an antigen such that antigen-containing vesicles are formed. The lyophilized lipid product is prepared by dissolving vesicle-forming lipids in a polar-protic water-miscible organic solvent to produce a lipid solution and then lyophilizing the lipid solution. In some embodiments, the vesicle-forming lipids are dissolved in a polar-protic water-miscible organic solvent without any co-solvents. In some embodiments, the vesicle-forming lipids are dissolved in a polar-protic water-miscible organic solvent with one or more co-solvents. In some embodiments, the vesicle-forming lipids are dissolved in a water-free solvent system.

In another aspect, the present disclosure provides antigen-containing vesicle formulations prepared using these methods. In some embodiments, the antigen-containing vesicle formulations exhibit antigen entrapment levels that are higher than those obtainable using prior art methods. In some embodiments, the antigen-containing vesicle formulations exhibit antigen activity levels that are higher than those obtainable using prior art methods.

In yet another aspect, the present disclosure provides kits that include a lyophilized lipid product in a first container and an aqueous solution comprising an antigen in a second container. In some embodiments, the kit also includes instructions for mixing the contents of the two containers in order to produce antigen-containing vesicle formulations.

DEFINITIONS

Throughout the present disclosure, several terms are employed that are defined in the following paragraphs.

As used herein, the term "antigen" refers to a substance containing one or more epitopes (either linear, conformational or both) that can be recognized by an antibody. In certain embodiments, an antigen can be a virus, a polypeptide, a polynucleotide, a polysaccharide, etc. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. In certain embodiments, an antigen may be an "immunogen."

As used herein, the term "entrapping" refers to any kind of physical association between a substance and a vesicle, e.g., encapsulation, adhesion (to the inner or outer wall of the vesicle) or embedding in the wall with or without extrusion of the substance. The term is used interchangeably with the terms "loading" and "containing".

As used herein, the terms "immune response" refer to a response elicited in an animal. An immune response may refer to cellular immunity, humoral immunity or may involve both. An immune response may also be limited to a part of the immune system. For example, in certain embodiments, an immunogenic formulation may induce an increased IFNγ response. In certain embodiments, an immunogenic formulation may induce a mucosal IgA response (e.g., as measured in nasal and/or rectal washes). In certain embodiments, an immunogenic formulation may induce a systemic IgG response (e.g., as measured in serum).

As used herein, the term "immunogenic" means capable of producing an immune response in a host animal against a non-host entity (e.g., a hepatitis A virus). In certain embodiments, this immune response forms the basis of the protective immunity elicited by a vaccine against a specific infectious organism (e.g., a hepatitis A virus). An "immunogen" is an immunogenic substance (e.g., a molecule).

As used herein, the terms "therapeutically effective amount" refer to the amount sufficient to show a meaningful benefit in a patient being treated. The therapeutically effective amount of an immunogenic formulation may vary depending on such factors as the desired biological endpoint, the nature of the formulation, the route of administration, the health, size and/or age of the patient being treated, etc.

As used herein, the term "polypeptide" refers to a protein (i.e., a string of at least two amino acids linked to one another by peptide bonds). In some embodiments, polypeptides may include moieties other than amino acids (e.g., may be glycoproteins, proteoglycans, lipoproteins, etc.) and/or may be otherwise processed or modified. Those of ordinary skill in the art will appreciate that a "protein" can be a complete polypeptide chain as produced by a cell (with or without a signal sequence), or can be a portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise natural amino acids, non-natural amino acids, synthetic amino acids, and combinations thereof.

As used herein, the term "polysaccharide" refers to a polymer of sugars. The polymer may include natural sugars (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified sugars (e.g., 2'-fluororibose, 2'-deoxyribose, and hexose). Exemplary polysaccharides include starch, glycogen, dextran, cellulose, etc.

As used herein, the term "polynucleotide" refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

As used herein, the term "small molecule therapeutic" refers to a non-polymeric therapeutic molecule that may contain several carbon-carbon bonds and have a molecular weight of less than about 1500 Da (e.g., less than about 1000 Da, less than about 500 Da or less than about 200 Da). A small molecule therapeutic can be synthesized in a laboratory (e.g., by combinatorial synthesis, using an engineered microorganism, etc.) or can be found in nature (e.g., a natural product). In general, a small molecule therapeutic may alter, inhibit, activate, or otherwise affect a biological event. For example, small molecule therapeutics may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary small molecules suitable for use in the methods of the present disclosure may be found in *Pharmaceutical Substances: Syntheses, Patents, Applications*, Edited by Axel Kleemann and Jurgen Engel, Thieme Medical Publishing, 1999; *Merck Index: An Encyclopedia of Chemicals, Drugs, and Biologicals*, Edited by Susan Budavari et al., CRC Press, 1996, and the *United States Pharmacopeia-25/National formulary-20*, published by the United States Pharmacopeial Convention, Inc., 2001. Preferably, though not necessarily, the small molecule is one that has already been deemed safe and effective for use by the appropriate governmental agency or body. For example, drugs for human use listed by the FDA under 21 C.F.R. §§ 330.5, 331 through 361, and 440 through 460 and drugs for veterinary use listed by the FDA under 21 C.F.R. §§ 500 through 589, are all considered acceptable for use in accordance with the methods of the present disclosure.

As used herein, the term "treat" (or "treating", "treated", "treatment", etc.) refers to the administration of a formulation to a patient who has a disease, a symptom of a disease or a predisposition toward a disease, with the purpose to alleviate, relieve, alter, ameliorate, improve or affect the disease, a symptom or symptoms of the disease, or the predisposition toward the disease. In certain embodiments, the term "treating" refers to the vaccination of a patient.

DETAILED DESCRIPTION OF SOME EMBODIMENTS

I. Methods for Preparing Vesicles

In one aspect, the present disclosure provides methods for preparing vesicles. Vesicles generally have an aqueous compartment enclosed by one or more bilayers which include lipids, optionally with other molecules. For example, as discussed in more detail below, in some embodiments, the vesicles of the present disclosure comprise transport enhancing molecules (e.g., bile salts) which facilitate the transport of lipids across mucosal membranes.

In general, the methods of the present disclosure include steps of providing a lyophilized lipid product and rehydrating the lyophilized lipid product with an aqueous solution comprising an antigen such that antigen-containing vesicles are formed. In some embodiments, the aqueous solution comprising an antigen is kept at a temperature range between about 25° C. and 50° C. In some embodiments, the aqueous solution comprising an antigen is kept at room temperature. The lyophilized lipid product is prepared by dissolving vesicle-forming lipids in a polar-protic water-miscible organic solvent to produce a lipid solution and then lyophilizing the lipid solution.

Without wishing to be bound to any theory, it is thought that by adding an aqueous solution of antigens to the lyophilized lipid product, vesicles are formed in the presence of the antigen. This may explain the high entrapment efficiencies observed. Additionally, in some embodiments, the methods of the present disclosure avoid exposing antigen to any organic solvent since it has been removed during the lyophilization process. Without wishing to be limited to any theory, this may explain the high activity (i.e., antigenicity and/or immunogenicity) of the entrapped antigens in the resulting formulations.

Vesicle-Forming Lipids

Lipids are organic molecules that are generally insoluble in water but soluble in nonpolar organic solvents (e.g., ether, chloroform, acetone, benzene, etc.). Fatty acids are one class of lipids that include an acid moiety linked to a saturated or unsaturated hydrocarbon chain. Specific examples include lauric acid, palmitic acid, stearic acid, arachidic acid, palmitoleic acid, oleic acid, linoleic acid, linolenic acid, arachidonic acid, etc. Alkali metal salts of fatty acids are typically more soluble in water than the acids themselves. Fatty acids and their salts that include hydrocarbon chains with eight or more carbons often exhibit amphiphilic properties due to the presence of both hydrophilic (head) and hydrophobic (tail) regions in the same molecule. Non-ionic lipids that include polar head groups can also exhibit amphiphilic (i.e., surfactant) properties. The triesters of fatty acids with glycerol (1,2,3-trihydroxypropane) compose another class of lipids known as triglycerides that are commonly found in animal fats and plant oils. Esters of fatty acids with long chain monohydric alcohols form another class of lipids that are found in waxes. Phospholipids are yet another class of lipids. They resemble the triglycerides in being ester or amide derivatives of glycerol or sphingosine with fatty acids and phosphoric acid. The phosphate moiety of the resulting phosphatidic acid may be further esterified with ethanolamine, choline or serine in the phospholipid itself. It is to be understood that the methods of the present disclosure may be used with any lipid that is capable of forming vesicles including any of the lipids that are described in the prior art (e.g., in *Liposome Technology*, 3rd Edition, Edited by Gregory Gregoriadis, Informa HealthCare, 2006 and *Liposomes: A Practical Approach* (*The Practical Approach Series*, 264), 2nd Edition, Edited by Vladimir Torchilin and Volkmar Weissig, Oxford University Press, USA, 2003).

In some embodiments, the vesicle-forming lipid is a phospholipid. Any naturally occurring or synthetic phospholipid can be used. Without limitation, examples of specific phospholipids are L-α-(distearoyl) lecithin, L-α-(dipalmitoyl) lecithin, L-α-phosphatide acid, L-α-(dilauroyl)-phosphatidic acid, L-α(dimyristoyl) phosphatidic acid, L-α(dioleoyl)phosphatidic acid, DL-α(dipalmitoyl) phosphatidic acid, L-α(distearoyl) phosphatidic acid, and the various types of L-α-phosphatidylcholines prepared from brain, liver, egg yolk, heart, soybean and the like, or synthetically, and salts thereof.

In some embodiments, the vesicle-forming lipid is a non-ionic surfactant. Non-ionic surfactant vesicles are referred to herein as "NISVs". Without limitation, examples of suitable non-ionic surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$ alkanoyl or alkenoyl moiety, for example caproyl, lauroyl, myristoyl, palmitoyl, oleyl or stearoyl. An exemplary non-ionic surfactant is 1-monopalmitoyl glycerol.

In some embodiments, ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$ alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monoacetyl glycerol ether and diglycolcetyl ether.

Polar Erotic Water-Miscible Organic Solvent

As mentioned above, the lyophilized lipid product is generally prepared by dissolving vesicle-forming lipids in a polar-protic water-miscible organic solvent to produce a lipid solution and then lyophilizing the lipid solution.

Protic solvents are solvents that contain dissociable protons (e.g., a hydrogen atom bound to an oxygen as in a hydroxyl group or a nitrogen as in an amine group). In some embodiments, the polar-protic water-miscible organic solvent is an aliphatic alcohol having 3-5 carbon atoms (e.g., 4 carbon atoms). In some embodiments, the solvent is tert-butanol.

In some embodiments, the vesicle-forming lipids are dissolved in a polar-protic water-miscible organic solvent without any co-solvents present. In some embodiments, the vesicle-forming lipids are dissolved in a polar-protic water-miscible organic solvent with one or more co-solvents present. In some embodiments one or more of the co-solvents are also polar-protic water-miscible organic solvents. In some embodiments, the polar-protic water-miscible organic solvent makes up at least 70% v/v of the solvent system, e.g., at least 75%, 80%, 90%, 95% or 99%. In some embodiments, the vesicle-forming lipids are dissolved in a water-free solvent system. In some embodiments, the vesicle-forming lipids are dissolved in a solvent system that includes an amount of water such that vesicles do not form.

In some embodiments, the vesicle-forming lipids are dissolved in a solvent system that includes less than 5% v/v water, e.g., less than 4%, 3%, 2%, 1%, 0.5%, or 0.1%.

Other Components

In some embodiments, the vesicles may contain other lipid and non-lipid components, as long as these do not prevent vesicle formation. It is to be understood that these components may be co-mixed with the vesicle-forming lipids and/or may be co-mixed with the antigen(s). In some embodiments, we have found that it can be advantageous to co-mix these components with the vesicle-forming lipids.

In some embodiments, the vesicles may include a transport enhancing molecule which facilitates the transport of lipids across mucosal membranes. As described in U.S. Pat. No. 5,876,721, a variety of molecules may be used as transport enhancers. For example, cholesterol derivatives in which the $C_{23}$ carbon atom of the side chain carries a carboxylic acid, and/or derivatives thereof, may be used as transport enhancers. Such derivatives include, but are not limited to, the "bile acids" cholic acid and chenodeoxycholic acid, their conjugation products with glycine or taurine such as glycocholic and taurocholic acid, derivatives including deoxycholic and ursodeoxycholic acid, and salts of each of these acids. NISVs that further include a bile acid or salt are referred to herein as "bilosomes". In some embodiments, transport enhancers include acyloxylated amino acids, such as acylcarnitines and salts thereof. For example, acylcarnitine containing $C_{6-20}$ alkanoyl or alkenoyl moieties, such as palmitoylcarnitine, may be used as transport enhancers. As used herein, the term acyloxylated amino acid is intended to cover primary, secondary and tertiary amino acids as well as $\alpha$, $\beta$, and $\gamma$ amino acids. Acylcarnitines are examples of acyloxylated $\gamma$ amino acids. It is to be understood that vesicles may comprise more than one type of transport enhancer, e.g., one or more different bile salts and one or more acylcarnitines. The transport enhancer(s), if present, will typically comprise between 40 and 400% percent by weight of the vesicle-forming lipid (e.g., between 60 and 100% by weight or between 70 and 90% by weight). In some embodiments, the transport enhancer(s), if present will comprise between 1 and 40% percent by weight of the vesicle-forming lipid (e.g., between 1 and 20% by weight, between 1 and 25% by weight, between 1 and 30% by weight, between 1 and 35% by weight, between 2 and 25% by weight, between 2 and 30% by weight or between 2 and 35% by weight).

In certain embodiments, the vesicles may lack a transport enhancing molecule. In some embodiments, the vesicles may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles may lack acyloxylated amino acids, such as acylcarnitines and salts thereof, and palmitoylcarnitines.

In some embodiments, the vesicles may include an ionic surfactant, e.g., to cause the vesicles to take on a negative charge. For example, this may help to stabilize the vesicles and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphospate, or phosphatidic acid or phosphatidyl serine) and sulphate monoesters such as higher alkyl sulphates (e.g., cetylsulphate), may all be used for this purpose. The ionic surfactant(s), if present, will typically comprise, between 1 and 30% by weight of the vesicle-forming lipid. For example, between 2 and 20% by weight or between 5 and 15% by weight. In some embodiments, the ionic surfactant(s), if present, will comprise between 1 and 50% by weight of the vesicle-forming lipid (e.g., between 1 and 35% by weight, between 5 and 40% by weight, between 10 and 40% by weight, between 15 and 40% by weight, between 20 and 40% by weight, or between 20 and 35% by weight).

In some embodiments, the vesicles may include an appropriate hydrophobic material of higher molecular mass that facilitates the formation of bilayers (such as a steroid, e.g., a sterol such as cholesterol). In some embodiments, the presence of the steroid may assist in forming the bilayer on which the physical properties of the vesicle depend. The steroid, if present, will typically comprise between 20 and 120% by weight of the vesicle-forming lipid. For example, between 25 and 90% by weight or between 35 and 75% by weight. In some embodiments, the steroid, if present, will comprise between 25 and 95% by weight, between 25 and 105% by weight, between 35 and 95% by weight, or between 35 and 105% by weight of the vesicle-forming lipid.

In some embodiments, a lyoprotectant may be included in the solution. Exemplary lyoprotectants include sucrose, trehalose, polyethylene glycol (PEG), dimethyl-succinate buffer (DMS), bovine serum albumin (BSA), mannitol and dextran.

In some embodiments, vesicles of the present disclosure are bilosomes that further include an ionic surfactant or a steroid. In some embodiments, the bilosomes may include both an ionic surfactant and a steroid.

In some embodiments, vesicles of the present disclosure are non-ionic surfactant vesicles (NISVs) that lack a transport enhancing molecule and that further include an ionic surfactant or a steroid. In some embodiments, the vesicles may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicles may lack acyloxylated amino acids, such as acylcarnitines and salts thereof, and palmitoylcarnitines. In some embodiments, the NISVs may lack a transport enhancing molecule (e.g., any of the aforementioned molecules) and include both an ionic surfactant and a steroid.

Lyophilization

As discussed above and below, the methods of the present disclosure include a step of lyophilizing (whether of a lipid solution or of a formulation of antigen-containing vesicles). Lyophilization is an established method used to enhance the long-term stability of products. Enhancement of physical and chemical stability is thought to be accomplished by preventing degradation and hydrolysis. Lyophilization involves freezing the preparation in question and then reducing the surrounding pressure (and optionally heating the preparation) to allow the frozen solvent(s) to sublime directly from the solid phase to gas (i.e., drying phase). In certain embodiments, the drying phase is divided into primary and secondary drying phases.

The freezing phase can be done by placing the preparation in a container (e.g., a flask, eppendorf tube, etc.) and optionally rotating the container in a bath which is cooled by mechanical refrigeration (e.g., using dry ice and methanol, liquid nitrogen, etc.). In some embodiments, the freezing step involves cooling the preparation to a temperature that is below the eutectic point of the preparation. Since the eutectic point occurs at the lowest temperature where the solid and liquid phase of the preparation can coexist, maintaining the material at a temperature below this point ensures that sublimation rather than evaporation will occur in subsequent steps.

The drying phase (or the primary drying phase when two drying phases are used) involves reducing the pressure and optionally heating the preparation to a point where the solvent(s) can sublimate. This drying phase typically removes the majority of the solvent(s) from the preparation. It will be appreciated that the freezing and drying phases are not necessarily distinct phases but can be combined in any manner. For example, in certain embodiments, the freezing and drying phases may overlap.

A secondary drying phase can optionally be used to remove residual solvent(s) that was adsorbed during the freezing phase. Without wishing to be bound to any theory, this phase involves raising the temperature to break any physico-chemical interactions that have formed between the solvent molecules and the frozen preparation. Once the drying phase is complete, the vacuum can be broken with an inert gas (e.g., nitrogen or helium) before the lyophilized lipid product is optionally sealed.

In some embodiments, the lyophilized lipid product is substantially free of organic solvent(s).

Rehydration

Once the lipid solution has been lyophilized the methods of the present disclosure include a step of rehydrating the lyophilized lipid product to form antigen-containing vesicles. This is achieved by mixing the lyophilized lipid product with an aqueous solution comprising an antigen. In some embodiments, this involves adding the aqueous solution to the lyophilized lipid product.

In some embodiments, the antigen-containing vesicles contain at least about 10% of the antigen added in the step of rehydrating. In some embodiments, the antigen-containing vesicles contain at least about 20% of the antigen added in the step of rehydrating. In some embodiments, the antigen-containing vesicles contain at least about 30% of the antigen added in the step of rehydrating. In some embodiments, the antigen-containing vesicles contain at least about 40% of the antigen added in the step of rehydrating. In some embodiments, the antigen-containing vesicles contain at least about 50% of the antigen added in the step of rehydrating. In some embodiments, the antigen-containing vesicles contain at least about 60% of the antigen added in the step of rehydrating. In some embodiments, the antigen-containing vesicles contain at least about 70% of the antigen added in the step of rehydrating. In some embodiments, the antigen-containing vesicles contain at least about 80% of the antigen added in the step of rehydrating. In some embodiments, the antigen-containing vesicles contain at least about 90% of the antigen added in the step of rehydrating.

In some embodiments, the aqueous solution includes a buffer. The buffer used will typically depend on the nature of the antigen or antigens in the aqueous solution. For example, without limitation, a PCB buffer, an $Na_2HPO_4/NaH_2PO_4$ buffer, a PBS buffer, a bicine buffer, a Tris buffer, a HEPES buffer, a MOPS buffer, etc. may be used. PCB buffer is produced by mixing sodium propionate, sodium cacodylate, and bis-Tris propane in the molar ratios 2:1:2. Varying the amount of HCl added enables buffering over a pH range from 4-9. In some embodiments, a carbonate buffer may be used.

In some embodiments, a formulation of antigen-containing vesicles prepared by any of the aforementioned methods may be lyophilized for future use and subsequently rehydrated (e.g., with sterile water or an aqueous buffer) prior to use. In some embodiments, an adjuvant may be added during this rehydration step (e.g., by inclusion in the sterile water or aqueous buffer). In some embodiments, a formulation of antigen-containing vesicles may be stored at −80° C. prior to lyophilization. In some embodiments, a lyophilized formulation may be stored at a range of temperatures between −20° C. and 10° C. (e.g., between −5° C. and 10° C., between 0° C. and 5° C. or between 2° C. and 8° C.).

Vesicle Size and Processing

It will be appreciated that a vesicle formulation will typically include a mixture of vesicles with a range of sizes. It is to be understood that the diameter values listed below correspond to the most frequent diameter within the mixture. In some embodiments >90% of the vesicles in a formulation will have a diameter which lies within 50% of the most frequent value (e.g., 1000±500 nm). In some embodiments the distribution may be narrower, e.g., >90% of the vesicles in a formulation may have a diameter which lies within 40, 30, 20, 10 or 5% of the most frequent value. In some embodiments, sonication or ultra-sonication may be used to facilitate vesicle formation and/or to alter vesicle particle size. In some embodiments, filtration, dialysis and/or centrifugation may be used to adjust the vesicle size distribution.

In general, vesicles produced in accordance with the methods of the present disclosure may be of any size. In some embodiments, the formulations may include vesicles with a diameter in the range of about 150 nm to about 15 µm, e.g., about 800 nm to about 1.5 µm. In certain embodiments, the vesicles may have a diameter which is greater than 10 µm, e.g., about 15 µm to about 25 µm. In certain embodiments, the vesicles may have a diameter in the range of about 2 µm to about 10 µm, e.g., about 1 µm to about 4 µm. In certain embodiments, the vesicles may have a diameter which is less than 150 nm, e.g., about 50 nm to about 100 nm.

Antigens

In general it is to be understood that any antigen or antigens may be entrapped using a method of the present disclosure. As previously discussed, the antigen or antigens may be associated with vesicles in any manner. In some embodiments, the antigen or antigens may be present in the aqueous core of the vesicles. However, depending on its hydrophobicity, an antigen may also be partially or completely associated with a bilayer. In general it is also to be understood that in some embodiments, a vesicle formulation may include amounts of one or more antigens that are not associated with vesicles.

In some embodiments, the methods of the present disclosure may be used to entrap one or more of the antigens included in a vaccine. Table 1 is a non-limiting list of suitable vaccines.

TABLE 1

| Vaccine | Disease |
| --- | --- |
| BioThrax ® | Anthrax |
| DTaP (Daptacel ®, Infanrix ®, Tripedia ®) | Diphtheria |
| Td (Decavac ®) | Diphtheria |
| DT, TT | Diphtheria |
| Tdap (Boostrix ®, Adacel ®) | Diphtheria |
| DTaP/IPV/HepB (Pediarix ®) | Diphtheria |
| DTaP/Hib (TriHIBit ®) | Diphtheria |
| HepA (Havrix ®, Vaqta ®) | Hepatitis A |
| HepA/HepB (Twinrix ®) | Hepatitis A |
| HepB/Hib (Comvax) | Hepatitis B |

TABLE 1-continued

| Vaccine | Disease |
|---|---|
| DTaP/IPV/HepB (Pediarix), | Hepatitis B |
| HepA/HepB (Twinrix ®) | Hepatitis B |
| Hib (ActHIB ®, HibTITER ®, PedvaxHIB ®) | HIB |
| HepB/Hib (Comvax ®) | HIB |
| DTaP/Hib (TriHIBit ®) | HIB |
| HPV (Gardasil ®) | HPV |
| Influenza (Fluarix ®, Fluvirin ®, Fluzone ®, Flulaval ®, FluMist ®) | Seasonal influenza |
| Influenza (Afluria ®) | Seasonal influenza |
| Influenza (Agriflu ®) | Seasonal influenza |
| Influenza (Begrivac ®) | Seasonal influenza |
| Influenza (Enzira ®) | Seasonal influenza |
| Influenza (Fluad ®) | Seasonal influenza |
| Influenza (Fluvax ®) | Seasonal influenza |
| Influenza (Fluviral, Fluviral S/F ®) | Seasonal influenza |
| Influenza (Grippol ®) | Seasonal influenza |
| Influenza (Inflexal, Inflexal S, Inflexal V ®) | Seasonal influenza |
| Influenza (Influvac ®) | Seasonal influenza |
| Influenza (Mastaflu ®) | Seasonal influenza |
| Influenza (Mutagrip ®) | Seasonal influenza |
| Influenza (Optaflu ®) | Seasonal influenza |
| Influenza (Vaxigrip ®) | Seasonal influenza |
| H1N1 pandemic influenza (Arepanrix ®) | H1N1 pandemic influenza |
| H1N1 pandemic influenza (Calvapan ®) | H1N1 pandemic influenza |
| H1N1 pandemic influenza (Focetria ®) | H1N1 pandemic influenza |
| H1N1 pandemic influenza (Influenza A (H1N1) 2009 Monovalent Vaccine ®) | H1N1 pandemic influenza |
| H1N1 pandemic influenza (Pandemrix ®) | H1N1 pandemic influenza |
| JE (JE-Vax ®) | Japanese Encephalitis |
| Lyme Disease (LYMErix ®) | Lyme Disease |
| Measles (Attenuvax ®) | Measles |
| MMR (M-M-R II ®) | Measles |
| MMRV (ProQuad ®) | Measles |
| Mening. Conjugate (Menactra ®) | Meningococcal |
| Mening. Polysaccharide (Menomune ®) | Meningococcal |
| Mumps (Mumpsvax ®) | Mumps |
| MMR (M-M-R II ®) | Mumps |
| MMRV (ProQuad ®) | Mumps |
| DTaP (Daptacel ®, Infanrix ®, Tripedia ®) | Pertussis |
| Tdap (Boostrix ®) | Pertussis |
| DTaP/IPV/HepB (Pediarix ®) | Pertussis |
| DTaP/Hib (TriHIBit ®) | Pertussis |
| Pneumo. Conjugate (Prevnar ®) | Pneumococcal |
| Pneumo. Polysaccharide (Pneumovax 23 ®) | Pneumococcal |
| Polio (Ipol ®) | Polio |
| DTaP/IPV/HepB (Pediarix ®) | Polio |
| Rabies (BioRab ®, Imovax Rabies ®, RabAvert ®) | Rabies |
| Rotavirus (RotaTeq ®) | Rotavirus |
| Rubella (Meruvax II ®) | Rubella |
| MMR (M-M-R II ®) | Rubella |
| MMRV (ProQuad ®) | Rubella |
| Shingles (Zostavax ®) | Shingles |
| Vaccinia (Dryvax ®) | Smallpox and Monkeypox |
| DTaP (Daptacel ®, Infanrix ®, Tripedia ®) | Tetanus |
| Td (Decavac ®) | Tetanus |
| DT, TT | Tetanus |
| Tdap (Boostrix ®) | Tetanus |
| DTaP/IPV/HepB (Pediarix ®) | Tetanus |
| DTaP/Hib (TriHIBit ®) | Tetanus |
| BCG | Tuberculosis |
| Typhoid (Typhim Vi ®) | Typhoid |
| Typhoid oral (Vivotif Berna ®) | Typhoid |
| Varicella (Varivax ®) | Chickenpox (Varicella) |
| MMRV (ProQuad ®) | Chickenpox (Varicella) |
| Yellow Fever (YF-Vax ®) | Yellow Fever |

In the following sections we discuss some exemplary antigens that could be used.

Hepatitis A

Hepatitis A is a serious liver disease caused by the hepatitis A virus (HAV). The virus is found in the stools of persons with hepatitis A. As shown in Table 1, several inactivated hepatitis A vaccines are currently licensed. For example, Havrix® is manufactured by GlaxoSmithKline Biologicals. U.S. Pat. No. 6,180,110 describes the attenuated HAV strain (HAV 4380) used in Havrix® which was originally derived from the HM175 strain of HAV (U.S. Pat. No. 4,894,228). Havrix® contains a sterile suspension of formalin inactivated HAV. The viral antigen activity is referenced to a standard using an ELISA and expressed in terms of ELISA Units (U). Each 1 ml adult dose of vaccine consists of 1440 U of viral antigen, adsorbed on 0.5 mg of aluminum as aluminum hydroxide (alum). Havrix® (as with all other licensed hepatitis A vaccines) is supplied as a sterile suspension for intramuscular (IM) administration. Although one dose of Havrix® provides at least short-term protection, a second booster dose after six to twelve months is currently recommended to ensure long-term protection.

Another example of an inactivated hepatitis A vaccine, AIMMUGEN® has been licensed and marketed in Japan since 1994 by Kaketsuken. AIMMUGEN® contains a sterile suspension of formaldehyde inactivated HAV. The recommended adult dose is 0.5 µg IM at 0, 1 and 6 months.

As used herein the expression "HAV antigen" refers to any antigen capable of stimulating neutralizing antibody to HAV in humans. The HAV antigen may comprise live attenuated virus particles or inactivated attenuated virus particles or may be, for example an HAV capsid or HAV viral protein, which may conveniently be obtained by recombinant DNA technology.

In one aspect, the present disclosure provides methods for preparing immunogenic formulations that include an inactivated or attenuated hepatitis A virus (also called "hepatitis A viral antigen" or "viral antigen" herein). It will be appreciated that the methods may be used to prepare an inactivated hepatitis A virus. In general, these methods will involve propagating a hepatitis A virus in a host cell, lyzing the host cell to release the virus, isolating and then inactivating the viral antigen. After removal of the cell culture medium, the cells are lysed to form a suspension. This suspension is purified through ultrafiltration and gel permeation chromatography procedures. The purified lysate is then treated with formalin to ensure viral inactivation (e.g., see Andre et al., Prog. Med. Virol. 37:72-95, 1990).

In preparing AIMMUGEN®, hepatitis A virus strain KRM0003 (established from a wild-type HAV, which had been isolated from the feces of a hepatitis A patient) is propagated in GL37 cells (a cell strain established for vaccine production from a parent cell strain of African green monkey kidney). The GL37 cells are inoculated with HAV strain KRM0003 and viral antigen is harvested, extensively purified and inactivated with formaldehyde.

Another example of an inactivated hepatitis A virus that is commercially available but is not a licensed vaccine is hepatitis A antigen (HAV-ag) from Meridian Life Sciences. Like Havrix® the Meridian HAV-ag also derives from hepatitis A virus strain HM175 but it is propagated in FRhK-4 (fetal rhesus kidney) cells. After removal of cell culture medium, the cells are lysed to form a suspension and the suspension is partially purified by gradient centrifugation and inactivated by treatment with formalin.

It will be appreciated that any hepatitis A virus strain may be used, e.g., without limitation any of the following strains which have been described in the art (and other non-human variants):

Human hepatitis A virus Hu/Arizona/HAS-15/1979
Human hepatitis A virus Hu/Australia/HM175/1976
Human hepatitis A virus Hu/China/H2/1982
Human hepatitis A virus Hu/Costa Rica/CR326/1960
Human hepatitis A virus Hu/France/CF-53/1979
Human hepatitis A virus Hu/Georgia/GA76/1976

Human hepatitis A virus Hu/Germany/GBM/1976
Human hepatitis A virus Hu/Japan/HAJ85-1/1985
Human hepatitis A virus Hu/Los Angelos/LA/1975
Human hepatitis A virus Hu/Northern Africa/MBB/1978
Human hepatitis A virus Hu/Norway/NOR-21/1998
Human hepatitis A virus Hu/Sierra Leone/SLF88/1988
Human hepatitis A virus MSM1
Human hepatitis A virus Shanghai/LCDC-1/1984

In addition, while formalin and formaldehyde are commonly used to inactivate licensed hepatitis A vaccines it is to be understood that other techniques could be used, e.g., treatment with chlorine, exposure to high temperatures (the viral antigen is inactivated above 85° C./185° F.), etc.

In certain embodiments it may prove advantageous to add additional steps to the traditional method for preparing an inactivated hepatitis A virus. For example, U.S. Pat. No. 6,991,929 describes including a protease treatment step (e.g., trypsin) after the virus has been propagated. This step was found to improve the removal of host cell material and yield a purer viral preparation.

While all currently licensed hepatitis A vaccines include inactivated viral antigens, alternative vaccines which include attenuated viral antigen have also been described in the literature. In certain embodiments, an immunogenic composition may comprise such an attenuated viral antigen. As is well known in the art, the advantage of an attenuated vaccine lies in the potential for higher immunogenicity which results from its ability to replicate in vivo without causing a full infection.

One method which has been used in the art to prepare attenuated hepatitis A viruses is viral adaptation which involves serially passing a viral strain through multiple cell cultures. Over time the strain mutates and attenuated strains can then be identified. In certain embodiments the virus may be passed through different cell cultures. For example, researchers have generated attenuated hepatitis A viruses by passing strain CR326 sixteen times in human diploid lung (MRCS) cell cultures (see Provost et al., *J. Med. Virol.* 20:165-175, 2005). A slightly more virulent strain was obtained by passing the same strain fifteen times in fetal rhesus monkey kidney (FRhK6) cell cultures plus eight times in MRCS cell cultures. An alternative attenuated hepatitis A vaccine which was prepared in this fashion from the H2 strain has also been described (see European Patent No. 0413637 and Mao et al., *Vaccine* 15:944-947, 1997).

In certain embodiments it may prove advantageous to perform one or more of the cell culture steps at a reduced temperature. For example, European Patent No. 0413637 describes including one or more inoculation steps in which the temperature is reduced (e.g., to 32-34° C. instead of 35-36° C.).

U.S. Pat. No. 6,180,110 describes an attenuated hepatitis A virus (HAV 4380) which grows in MRC-5 cells. The researchers identified mutations in HAV 4380 which appeared to be associated with attenuation by comparing its genome with the genome of a more virulent strain. This allowed them to design mutant HAV strains with optimal characteristics for a candidate attenuated hepatitis A vaccine. It will be appreciated that this approach could be applied to any known attenuated hepatitis A virus and used to genetically engineer variants without the need for viral adaptation.

Influenza

Influenza is a common infectious disease of the respiratory system associated with the Orthomyxoviridae family of viruses. Influenza A and B are the two types of influenza viruses that cause epidemic human disease. Influenza A viruses are further categorized into subtypes on the basis of two surface antigens: hemagglutinin (HA) and neuraminidase (N). Influenza B viruses are not categorized into subtypes. Vaccination is recognized as the single most effective way of preventing or attenuating influenza for those at high risk of serious illness from influenza infection and related complications. The inoculation of antigen prepared from inactivated influenza virus stimulates the production of specific antibodies. Protection is generally afforded only against those strains of virus from which the vaccine is prepared or closely related strains.

Influenza vaccines, of all kinds, are usually trivalent vaccines. They generally contain antigens derived from two influenza A virus strains and one influenza B strain. The influenza virus strains to be incorporated into influenza vaccines each season are determined by the World Health Organization (WHO) in collaboration with national health authorities and vaccine manufacturers. It will be appreciated that any influenza virus strain may be used in accordance with the present disclosure, and that influenza virus strains will differ from year to year based on WHO recommendations.

Monovalent vaccines, which may be useful for example in a pandemic situation, are also encompassed. A monovalent, pandemic flu vaccine will most likely contain influenza antigen from a single A strain. In some embodiments, influenza antigens are derived from pandemic influenza strains. For example, in some embodiments, influenza antigens are influenza A (H1N1 of swine origin) viral antigens.

Predominantly three types of inactivated vaccines are used worldwide to protect against influenza: whole virus vaccines, split virus vaccines containing external and internal components of the virus, and subunit vaccines composed of just external components of the virus (hemagglutinin and neuraminidase). Without wishing to be limited to any theory, it is thought that the higher purity of subunit vaccines should make them less reactogenic and better tolerated. Conversely whole virus and split virus vaccines are thought to contain more epitopes and so be more immunogenic.

In some embodiments, influenza antigens are based on subunit vaccines. Generally, subunit vaccines contain only those parts of the influenza virus that are needed for effective vaccination (e.g., eliciting a protective immune response). In some embodiments, subunit influenza antigens are prepared from virus particles (e.g., purification of particular components of the virus). In some embodiments, subunit influenza antigens are prepared by recombinant methods (e.g., expression in cell culture). For example, U.S. Pat. No. 5,858,368 describes methods of preparing a recombinant influenza vaccine using recombinant DNA technology. The resulting trivalent influenza vaccine is based on a mixture of recombinant hemagglutinin antigens cloned from influenza viruses having epidemic potential. The recombinant hemagglutinin antigens are full length, uncleaved, glycoproteins produced from baculovirus expression vectors in cultured insect cells and purified under non-denaturing conditions. In some embodiments, subunit influenza antigens are generated by synthetic methods (e.g., peptide synthesis). Subunit vaccines may contain purified surface antigens, hemagglutinin antigens and neuraminidase antigens prepared from selected strains determined by the WHO. Without wishing to be bound by any theories, it is thought that surface antigens, hemagglutinin antigens and neuramidase antigens play a significant role in eliciting production of virus neutralizing antibodies upon vaccination.

In some embodiments, influenza antigens are split virus antigens. Vaccines prepared using split virus antigens typically contain a higher concentration of the most immunogenic portions of the virus (e.g., hemagglutinin and neuramidase), while lowering the concentration of less immunogenic viral proteins as well as non-viral proteins present from eggs (used to produce virus) or extraneous agents (e.g., avian leukosis virus, other microorganisms and cellular debris). Generally, split virus antigens are prepared by a physical process that involves disrupting the virus particle, generally with an organic solvent or a detergent (e.g., Triton X-100), and separating or purifying the viral proteins to varying extents, such as by centrifugation over a sucrose gradient or passage of allantoic fluid over a chromatographic column. In some embodiments, disruption and separation of virus particles is followed by dialysis or ultrafiltration. Split virus antigens usually contain most or all of the virus structural proteins although not necessarily in the same proportions as they occur in the whole virus. Methods of viral splitting as well as suitable splitting agents are known in the art (see for example U.S. Patent Publication No. 20090155309). In some embodiments, final antigen concentration (e.g., of hemagglutinin and/or neuramidase antigens) of split viral antigen is standardized using methods known in the art (e.g., ELISA).

In some embodiments, influenza antigens are whole virus antigens. It is thought that in unprimed individuals, vaccines prepared with whole virus antigens may be more immunogenic and induce higher protective antibody response at a lower antigen dose that other formulations (e.g., subunit or split virus antigens). However, influenza vaccines that include whole virus antigens can produce more side effects than other formulations.

Influenza viral antigens present in immunogenic formulations described herein may be infectious, inactivated or attenuated.

In certain embodiments, an immunogenic formulation may comprise an inactivated viral antigen. It will be appreciated that any method may be used to prepare an inactivated influenza viral antigen. WO 09/029,695 describes exemplary methods for producing a whole inactivated virus vaccine. In general, these methods will involve propagating an influenza virus in a host cell, optionally lysing the host cell to release the virus, isolating and then inactivating the viral antigen. Chemical treatment of virus (e.g., formalin, formaldehyde, among others) is commonly used to inactivate virus for vaccine formulation. However, it is to be understood that other techniques could be used, e.g., treatment with chlorine, exposure to high temperatures, etc. In these treatments the outer virion coat is typically left intact while the replicative function is impaired. Non-replicating virus vaccines preferably contain more antigen than live vaccines that are able to replicate in the host.

In certain embodiments, an immunogenic formulation may comprise an attenuated viral antigen. As is well known in the art, one advantage of a vaccine prepared with an attenuated viral antigen lies in the potential for higher immunogenicity which results from its ability to replicate in vivo without causing a full infection. Live virus vaccines that are prepared from attenuated strains preferably lack pathogenicity but are still able to replicate in the host. One method which has been used in the art to prepare attenuated influenza viral antigens is viral adaptation which involves serially passing a viral strain through multiple cell cultures. Over time the strain mutates and attenuated strains can then be identified. In certain embodiments the virus may be passed through different cell cultures. In certain embodiments it may prove advantageous to perform one or more of the cell culture steps at a reduced temperature.

Several influenza vaccines are currently licensed (see Table 1). For example, Fluzone®, which is a split cell inactivated influenza vaccine, is developed and manufactured by Sanofi Pasteur, Inc. and may be used in accordance with the present disclosure. Fluzone® contains a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100) producing a split viral antigen. The split virus is then further purified by chemical means and suspended in sodium phosphate-buffered isotonic sodium chloride solution. Fluzone® vaccine is then standardized according to requirements for the influenza season and is formulated to contain 45 μg hemagglutinin (HA) per 0.5 mL dose, in the recommended ratio of 15 μg HA each, representative of the three prototype strains (e.g., 2007-2008 vaccine prepared with A/Solomon Islands/3/2006 (H1N1), A/Wisconsin/67/2005 (H3N2) and B/Malaysia/2506/2004 strains). Fluzone® vaccine is formulated for intramuscular injection.

Another example of a licensed influenza vaccine that may be used in accordance with the present disclosure is Vaxigrip®, which is a split cell inactivated influenza vaccine also developed and manufactured by Sanofi Pasteur, Inc. Vaxigrip® is prepared in a similar fashion to the process outlined above for Fluzone® and is similarly formulated for intramuscular injection.

Yet another example of a licensed influenza vaccine that may be used in accordance with the present disclosure is Flumist®. Flumist® is a live, attenuated trivalent vaccine for administration by intranasal spray. The influenza virus strains in Flumist® have three genetic mutations that lead to temperature restricted growth and an attenuated phenotype. The cumulative effect of the antigenic properties and the genetically modified influenza viruses is that they are able to replicate in the nasopharynx and induce protective immunity. In order to produce Flumist®, specific pathogen-free (SPF) eggs are inoculated with each of the appropriate viral strains and incubated to allow vaccine virus replication. The allantoic fluid of these eggs is harvested, pooled and then clarified by filtration. The virus is concentrated by ultracentrifugation and diluted with stabilizing buffer to obtain the final sucrose and potassium phosphate concentrations. Viral harvests are then sterile filtered to produce the monovalent bulks. Monovalent bulks from the three strains are subsequently blended and diluted as required to attain the desired potency with stabilizing buffers to produce the trivalent bulk vaccine. The bulk vaccine is then filled directly into individual sprayers for nasal administration. Each pre-filled refrigerated Flumist® sprayer contains a single 0.2 mL dose. Each 0.2 mL dose contains $10^{6.5-7.5}$ FFU of live attenuated influenza virus reassortants of each of the appropriate three viral strains.

As described above, several influenza vaccines are currently licensed. It is to be understood that any one or combination of these licensed influenza vaccines may be combined with a vesicle as described herein to produce an immunogenic formulation. For example, commercial Fluzone® and/or Vaxigrip® may be combined in this manner to produce an active immunogenic formulation. In some embodiments, licensed influenza vaccines are first purified (e.g., to remove alum adjuvant or other reagents in the vaccine). In some embodiments, licensed influenza vaccines are not purified prior to formulation with a vesicle as described herein.

PCT Patent Application No. PCT/US09/47911 describes some other exemplary influenza antigens that could be used in the methods and formulations of the present disclosure. Exemplary influenza antigens have also been described in U.S. Pat. Nos. 7,527,800; 7,537,768; 7,514,086; 7,510,719; 7,494,659; 7,468,259; 7,399,840; 7,361,352; 7,316,813; 7,262,045; 7,244,435; 7,192,595; 7,052,701; 6,861,244; 6,743,900; 6,740,325; 6,635,246; 6,605,457; 6,534,065; 6,372,223; 6,344,354; 6,287,570; 6,136,606; 5,962,298; 5,948,410; and 5,919,480.

Other Viruses

Hepatitis C virus (HCV) is now recognized as being the primary cause of transfusion-associated non-A, non-B (NANB) hepatitis. HCV is a single stranded, positive sense RNA virus with similarities to flaviviruses and pestiviruses (Miller et al., *Proc. Natl. Acad. Sci.* 87: 2057, 1991 and Weiner et al., *Virology* 180: 842, 1990). U.S. Pat. Nos. 7,348,011; 6,831,169; 6,538,123 and 6,235,888 all describe exemplary HCV antigens that could be employed in a vaccine.

The human immunodeficiency retrovirus (HIV) is responsible for AIDS (acquired immunodeficiency syndrome), a disease in which the body's immune system breaks down leaving it vulnerable to opportunistic infections. U.S. Pat. Nos. 7,067,134; 7,063,849; 6,787,351; 6,706,859; 6,692,955; 6,653,130; 6,649,410; 6,541,003; 6,503,753; 6,500,623; 6,383,806; 6,090,392; 5,861,243; 5,817,318; and 4,983,387 all describe exemplary HIV antigens that could be employed in a vaccine. Various HIV antigens are also disclosed in U.S. Patent Application Publication Nos. 20090117141 and 20090081254.

In certain embodiments, an immunogenic formulation that is prepared in accordance with the methods of the present disclosure may comprise an antigen that is sensitive to exposure to organic solvent. In some embodiments, an antigen may lose antigenic integrity when exposed to certain organic solvents (e.g., polar protic solvents). In some embodiments, exposure of an antigen to organic solvent destroys over 20% of the antigenic integrity of the antigen (e.g., over 30%, over 40%, over 50% or more) as measured in an antigenic integrity assay (e.g., an ELISA) as compared to the un-manipulated antigen. In certain embodiments, an antigen loses antigenic integrity when exposed to organic solvent for more than 3 minutes (e.g., 5 minutes, 10 minutes, 15 minutes or more) destroys over 20% of the antigenic integrity of the antigen (e.g., over 30%, over 40%, over 50% or more) as measured in an antigenic integrity assay (e.g., an ELISA) as compared to the un-manipulated antigen. As discussed above, methods of the present disclosure are particularly beneficial for antigens that are sensitive to exposure to organic solvents because they avoid exposure of the antigen solution to organic solvent, allowing for better preservation of antigenic integrity.

It is to be understood that the present disclosure is not limited to antigens and that, in general, the methods may be used to entrap any substance whether antigenic or non-antigenic. Therefore, in some embodiments, the methods of the present disclosure may be used to entrap one or more polypeptides, polynucleotides or polysaccharides that may or may not be antigenic. Specific classes of substances include, but are not limited to, adjuvants, enzymes, receptors, neurotransmitters, hormones, cytokines, cell response modifiers such as growth factors and chemotactic factors, antibodies, haptens, toxins, interferons, ribozymes, anti-sense agents, plasmids, DNA, and RNA. In some embodiments the polypeptide may be an antibody or antibody fragment, e.g., a humanized antibody. In some embodiments, these substances are sensitive to exposure to organic solvents.

Adjuvants

In certain embodiments, the methods of the present disclosure may further include a step of adding one or more adjuvants to a vesicle formulation. As is well known in the art, adjuvants are agents that enhance immune responses. Adjuvants are well known in the art (e.g., see "Vaccine Design: The Subunit and Adjuvant Approach", *Pharmaceutical Biotechnology*, Volume 6, Eds. Powell and Newman, Plenum Press, New York and London, 1995). In some embodiments, an adjuvant may be added once the vesicle formulation (with entrapped antigen) has been prepared. In some embodiments, an adjuvant may be added during the process of preparing the vesicle formulations (e.g., along with other vesicle components, along with the antigen or in a dedicated step).

In certain embodiments, an adjuvant is added before antigen is added. In some embodiments, adjuvant is co-mixed with vesicle-forming lipids. In some embodiments, lyophilized lipid product comprises adjuvant. In certain embodiments, an adjuvant is added after an antigen is added. In some embodiments, adjuvant is added along with a lyoprotectant after antigen is added.

Exemplary adjuvants include complete Freund's adjuvant (CFA), incomplete Freund's adjuvant (IFA), squalene, squalane and alum (aluminum hydroxide), which are materials well known in the art, and are available commercially from several sources. In certain embodiments, aluminum or calcium salts (e.g., hydroxide or phosphate salts) may be used as adjuvants. Alum (aluminum hydroxide) has been used in many existing vaccines. Typically, about 40 to about 700 µg of aluminum is included per dose when given IM. For example, Havrix® includes 500 µg of aluminum per dose.

In various embodiments, oil-in-water emulsions or water-in-oil emulsions can also be used as adjuvants. For example, the oil phase may include squalene or squalane and a surfactant. In various embodiments, non-ionic surfactants such as the mono- and di-$C_{12}$-$C_{24}$-fatty acid esters of sorbitan and mannide may be used. The oil phase preferably comprises about 0.2 to about 15% by weight of the immunogenic formulation (e.g., about 0.2 to 1%). PCT Publication No. WO 95/17210 describes exemplary emulsions.

The adjuvant designated QS21 is an immunologically active saponin fractions having adjuvant activity derived from the bark of the South American tree Quillaja Saponaria Molina, and the methods of its production is disclosed in U.S. Pat. No. 5,057,540. Semi-synthetic and synthetic derivatives of Quillaja Saponaria Molina saponins are also useful, such as those described in U.S. Pat. Nos. 5,977,081 and 6,080,725.

TLRs are a family of proteins homologous to the Drosophila Toll receptor, which recognize molecular patterns associated with pathogens and thus aid the body in distinguishing between self and non-self molecules. Substances common in viral pathogens are recognized by TLRs as pathogen-associated molecular patterns. For example, TLR-3 recognizes patterns in double-stranded RNA, TLR-4 recognizes patterns in lipopolysaccharides while TLR-7/8 recognize patterns containing adenosine in viral and bacterial RNA and DNA. When a TLR is triggered by such pattern recognition, a series of signaling events occurs that leads to inflammation and activation of innate and adaptive immune responses. A number of synthetic ligands containing the molecular patterns recognized by various TLRs are being developed as adjuvants and may be included in an immunogenic formulation as described herein.

For example, polyriboinosinic:polyribocytidylic acid or poly(I:C) (available from InvivoGen of San Diego, Calif.) is a synthetic analog of double-stranded RNA (a molecular pattern associated with viral infection) and an exemplary adjuvant that is an agonist for TLR-3 (e.g., see Field et al., *Proc. Natl. Acad. Sci. USA* 58:1004 (1967) and Levy et al., *Proc. Natl. Acad. Sci. USA* 62:357 (1969)). In some embodiments, poly(I:C) may be combined with other agents to improve stability (e.g., by reducing degradation via the activity of RNAses). For example, U.S. Pat. Nos. 3,952,097; 4,024,241 and 4,349,538 describe poly(I:C) complexes with poly-L-lysine. The addition of poly-arginine to poly(I:C) has also been shown to reduce degradation via the activity of RNAses. Poly(IC:LC) is a synthetic, double-stranded poly (I:C) stabilized with poly-L-lysine carboxymethyl cellulose. U.S. Patent Publication No. 20090041809 describes double-stranded nucleic acids with one or more than one locked nucleic acid (LNA) nucleosides that can act as TLR-3 agonists. Those skilled in the art will be able to identify other suitable TLR-3 agonist adjuvants.

Attenuated lipid A derivatives (ALD) such as monophosphoryl lipid A (MPL) and 3-deacyl monophosphoryl lipid A (3D-MPL) are exemplary adjuvants that are agonists for TLR-4. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$). MPL and 3D-MPL are described in U.S. Pat. Nos. 4,436,727 and 4,912,094, respectively. MPL was originally derived from lipid A, a component of enterobacterial lipopolysaccharides (LPS), a potent but highly toxic immune system modulator. 3D-MPL differs from MPL in that the acyl residue that is ester linked to the reducing-end glucosamine at position 3 has been selectively removed. It will be appreciated that MPL and 3D-MPL may include a mixture of a number of fatty acid substitution patterns, i.e., heptaacyl, hexaacyl, pentaacyl, etc., with varying fatty acid chain lengths. Thus, various forms of MPL and 3D-MPL, including mixtures thereof, are encompassed by the present disclosure.

In some embodiments these ALDs may be combined with trehalosedimycolate (TDM) and cell wall skeleton (CWS), e.g., in a 2% squalene/Tween™ 80 emulsion (e.g., see GB Patent No. 2122204). MPL is available from Avanti Polar Lipids, Inc. of Alabaster, Ala. as PHAD™ (phosphorylated hexaacyl disaccharide). Those skilled in the art will be able to identify other suitable TLR-4 agonist adjuvants. For example, other lipopolysaccharides have been described in PCT Publication No. WO 98/01139; U.S. Pat. No. 6,005,099 and EP Patent No. 729473.

II. Vesicle Formulations

In another aspect, the present disclosure provides antigen-containing vesicle formulations prepared using these methods. In some embodiments, the antigen-containing vesicle formulations exhibit antigen entrapment levels that are higher than those obtainable using prior art methods. In some embodiments, the antigen-containing vesicle formulations exhibit antigen activity (i.e., antigenicity and/or immunogenicity) levels that are higher than those obtainable using prior art methods.

Immunogenic vesicle formulations are useful for treating many diseases in humans including adults and children. In general however they may be used with any animal. In certain embodiments, the methods herein may be used for veterinary applications, e.g., canine and feline applications. If desired, the methods herein may also be used with farm animals, such as ovine, avian, bovine, porcine and equine breeds.

Immunogenic vesicle formulations described herein will generally be administered in such amounts and for such a time as is necessary or sufficient to induce an immune response. Dosing regimens may consist of a single dose or a plurality of doses over a period of time. The exact amount of antigen to be administered may vary from patient to patient and may depend on several factors. Thus, it will be appreciated that, in general, the precise dose used will be as determined by the prescribing physician and will depend not only on the weight of the patient and the route of administration, but also on the frequency of dosing, the age of the patient and the severity of the symptoms and/or the risk of infection. In certain embodiments, the dose of antigen in an immunogenic formulation may range from about 5 μg to about 5 mg, e.g., from about 100 μg to about 750 μg. Lower doses of antigen may be sufficient when using sublingual or buccal administration, or in the presence of adjuvant. Higher doses may be more useful when given orally, especially in the absence of adjuvants.

In general, the formulations may be administered to a patient by any route. In particular, the results in the Examples demonstrate that the immunogenic formulations described herein can induce a protective response even when administered orally. It will be appreciated that the oral route is particularly desirable in light of the advantages of oral delivery over any form of injection (i.e., compliance, mass distribution, etc.). It will also be appreciated that the results are unexpected in light of the fact that most vaccines (including all known hepatitis A vaccines) have so far been administered parenterally.

Thus, in certain embodiments, the immunogenic formulations may be administered orally (including buccally, sublingually and by gastric lavage or other artificial feeding means). Such oral delivery may be accomplished using solid or liquid formulations, for example in the form of tablets, capsules, multi-particulates, gels, films, ovules, elixirs, solutions, suspensions, etc. In certain embodiments, when using a liquid formulation, the formulation may be administered in conjunction with a basic formulation (e.g., a bicarbonate solution) in order to neutralize the stomach pH. In certain embodiments, the basic formulation may be administered before and/or after the immunogenic formulation. In certain embodiments, the basic formulation may be combined with the immunogenic formulation prior to administration or taken at the same time as the immunogenic formulation.

While oral delivery is of particular interest, it will be appreciated that in certain embodiments, an immunogenic formulation may also be formulated for delivery parenterally, e.g., by injection. In such embodiments, administration may be, for example, intravenous, intramuscular, intradermal, or subcutaneous, or via by infusion or needleless injection techniques. For such parenteral administration, the immunogenic formulations may be prepared and maintained in conventional lyophilized formulations and reconstituted prior to administration with a pharmaceutically acceptable saline solution, such as a 0.9% saline solution. The pH of the injectable formulation can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid formulations which can be dissolved or dispersed in sterile water or other sterile injectable medium prior to use.

The immunogenic formulations can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g., dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitantrioleate. Capsules and cartridges (made, for example, from gelatin) for use in an inhaler or insufflator may be formulated to contain a powder mix of the immunogenic formulation and a suitable powder base such as lactose or starch.

Formulations for rectal administration are preferably suppositories which can be prepared by mixing the immunogenic formulation with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the disclosure for rectal administration since they facilitate retention of the formulation within the rectum. Generally, the volume of carrier that is added to the formulation is selected in order to maximize retention of the formulation. In particular, the volume should not be so large as to jeopardize retention of the administered formulation in the rectal vault.

Exemplary Formulations

In some embodiments, the present disclosure provides immunogenic formulations that include an antigen, a TLR-3 agonist adjuvant and a vesicle which comprises a non-ionic surfactant and a transport enhancer which facilitates the transport of lipid-like molecules across mucosal membranes. In some embodiments, these formulations may be administered orally. In some embodiments the TLR-3 agonist adjuvant comprises poly(I:C). In some embodiments the TLR-3 agonist adjuvant comprises poly(IC:LC). In some embodiments, the transport enhancer is a bile acid, a derivative thereof or a salt of any of these (e.g., sodium deoxycholate). In some embodiments, the non-ionic surfactant is a glycerol ester (e.g., 1-monopalmitoyl glycerol). In some embodiments, the vesicle further comprises an ionic amphiphile (e.g., dicetylphospate). In some embodiments, the vesicle further comprises a steroid (e.g., cholesterol). In some embodiments, the vesicles comprise 1-monopalmitoyl glycerol, dicetylphospate, cholesterol and sodium deoxycholate.

In some embodiments, the present disclosure provides immunogenic formulations that include an antigen, a TLR-3 agonist adjuvant and a vesicle which comprises a non-ionic surfactant. In some embodiments, these formulations may be administered parenterally (e.g., by intramuscular injection). In some embodiments the TLR-3 agonist adjuvant comprises poly(I:C). In some embodiments the TLR-3 agonist adjuvant comprises poly(IC:LC). In some embodiments, the non-ionic surfactant is a glycerol ester (e.g., 1-monopalmitoyl glycerol). In some embodiments, the vesicle further comprises an ionic amphiphile (e.g., dicetylphosphate). In some embodiments, the vesicle further comprises a steroid (e.g., cholesterol). In some embodiments, the vesicles comprise 1-monopalmitoyl glycerol, dicetylphospate and cholesterol. In some embodiments, the vesicle may lack a transport enhancing molecule. In some embodiments, the vesicle may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicle may lack acyloxylated amino acids, such as acylcarnitines and salts thereof, and palmitoylcarnitines.

In some embodiments, the present disclosure provides immunogenic formulations that include an antigen, a TLR-4 agonist adjuvant and a vesicle which comprises a non-ionic surfactant and a transport enhancer which facilitates the transport of lipid-like molecules across mucosal membranes. In some embodiments, these formulations may be administered orally. In some embodiments the TLR-4 agonist adjuvant comprises monophosphoryl lipid A or 3-deacyl monophosphoryl lipid A. In some embodiments, the transport enhancer is a bile acid, a derivative thereof or a salt of any of these (e.g., sodium deoxycholate). In some embodiments, the non-ionic surfactant is a glycerol ester (e.g., 1-monopalmitoyl glycerol). In some embodiments, the vesicle further comprises an ionic amphiphile (e.g., dicetylphospate). In some embodiments, the vesicle further comprises a steroid (e.g., cholesterol). In some embodiments, the vesicles comprise 1-monopalmitoyl glycerol, dicetylphospate, cholesterol and sodium deoxycholate.

In some embodiments, the present disclosure provides immunogenic formulations that include an antigen, a TLR-4 agonist adjuvant and a vesicle which comprises a non-ionic surfactant. In some embodiments, these formulations may be administered parenterally (e.g., by intramuscular injection). In some embodiments the TLR-4 agonist adjuvant comprises monophosphoryl lipid A or 3-deacyl monophosphoryl lipid A. In some embodiments, the non-ionic surfactant is a glycerol ester (e.g., 1-monopalmitoyl glycerol). In some embodiments, the vesicle further comprises an ionic amphiphile (e.g., dicetylphospate). In some embodiments, the vesicle further comprises a steroid (e.g., cholesterol). In some embodiments, the vesicles comprise 1-monopalmitoyl glycerol, dicetylphospate and cholesterol. In some embodiments, the vesicle may lack a transport enhancing molecule. In some embodiments, the vesicle may lack a "bile acid" such as cholic acid and chenodeoxycholic acid, their conjugation products with glycine or taurine such as glycocholic and taurocholic acid, derivatives including deoxycholic and ursodeoxycholic acid, and salts of each of these acids. In some embodiments, the vesicle may lack acyloxylated amino acids, such as acylcarnitines and salts thereof, and palmitoylcarnitines.

In some embodiments, the present disclosure provides any one of the aforementioned formulations in a lyophilized form.

III. Kits

In yet another aspect, the present disclosure provides kits that include a lyophilized lipid product in a first container and an aqueous solution comprising an antigen (and optionally an adjuvant) in a second container. In some embodiments, the kit also includes instructions for mixing the contents of the first and second containers in order to produce antigen-containing vesicles.

As discussed above, the lyophilized lipid product is one that was previously prepared by dissolving vesicle-forming lipids in a polar-protic water-miscible organic solvent to produce a lipid solution and then lyophilizing the lipid solution.

In yet another aspect, the present disclosure provides kits that include any lyophilized antigen-containing vesicle formulation of the present disclosure in a first container and an aqueous solution (optionally containing an adjuvant) in a second container. In some embodiments, the kit also includes instructions for mixing the contents of the two containers in order to rehydrate the antigen-containing vesicle formulation.

In some embodiments, the kit may include additional components such as a syringe for injecting the antigen-containing vesicle formulation into a patient.

EXAMPLES

The following examples describe some exemplary modes of making and practicing certain formulations that are described herein. It should be understood that these examples are for illustrative purposes only and are not meant to limit the scope of the formulations and methods described herein.

Example 1: Antigen Entrapment

This example describes the preparation of hepatitis A vesicles without exposure to tert-butanol. A 5:4:1:0.5 molar ratio of 1-monopalmitoyl glycerol (270 mg), cholesterol (255 mg), dicetyl phosphate (90 mg) and sodium deoxycholate (32 mg) was placed in a round bottom flask, ensuring none of the powder stuck to the side of the glass flask. The mixture was then dissolved in 20 ml of tert-butanol with stirring and heat (35° C.) applied. Ten 2 ml aliquots of the lipid solution were subsequently lyophilized. Each vial was then re-suspended in 2 mls of an aqueous antigen solution (0.138 ml of 29 μg/ml Hep A in 1.862 ml of 20 mM $Na_2HPO_4/NaH_2PO_4$ buffer, pH 8.14). When preparing hepatitis A vesicles using this method we have been able to achieve significant entrapment efficiencies (data not shown).

Comparative experiments would involve preparing hepatitis A vesicles with exposure to tert-butanol as follows. A 5:4:1:0.5 molar ratio of 1-monopalmitoyl glycerol (270 mg), cholesterol (255 mg), dicetyl phosphate (90 mg) and sodium deoxycholate (32 mg) are placed in a round bottom flask, ensuring none of the powder stuck to the side of the glass flask. The mixture is then dissolved in 20 ml of tert-butanol with stirring and heat (35° C.) applied. While stirring, 20 ml of an aqueous antigen solution is added (1.38 ml of 29 μg/ml Hep A in 18.6 ml of 20 mM $Na_2HPO_4/NaH_2PO_4$ buffer, pH 8.14). Subsequently, ten 4 ml aliquots are lyophilized. The vesicles are then rehydrated by re-suspending each vial in 2 ml of sterile water.

Example 2: Antigen Activity

To demonstrate the improved value of the methods of the present disclosure on antigen activity we compared hepatitis A formulations prepared using an established melt-based method with formulations prepared using a method of the present disclosure (same method as Example 1). In the melt-based method, the vesicle-forming lipids were melted at high temperature (135° C.). An aqueous buffered antigen solution at 30° C. was then added to the molten lipids and homogenized. Mice were immunized by gastric gavage formulations containing an input amount of 1 μg of inactivated hepatitis A antigen in volumes of 200 μl. Mice were immunized 3 times on days 0, 14, and 28, and antibody (IgG) responses against hepatitis A antigen were tested in serum samples by ELISA. As shown in FIG. 1, the hepatitis A-specific antibody responses were far stronger when the vesicle formulations were prepared using a method of the present disclosure.

Example 3: Maturation of Immature Dendritic Cells

It is now generally accepted that dendritic cells (DC) are important antigen presenting cells that play a role in establishing whether an antigen (for example HAV antigen) induces tolerance or a protective immune response in the intestine (Alpan et al., *J. Immunol.* 166 (8): 4843-4852, 2001). Activation of DCs, usually by inflammatory stimuli, promotes the expression of co-stimulatory molecules and presentation of antigens in a manner that allows productive priming of T cells. The cytokine profile of activated DC seems to be important in establishing tolerance or a protective immune response, production of immunoregulatory cytokines seems to lead to immune tolerance while pro-inflammatory mediators lead to a protective immune response (Mowat, *Vaccine* 23: 1797-1799, 2005).

Briefly, bone marrow derived DC progenitors were isolated from naïve BALB/c mice and cultured in the presence of interleukin 4 (IL-4) and granulocyte-macrophage colony stimulating factor (GM-CSF) which leads to differentiation to the immature DC phenotype (5 days). Subsequent treatment with tumor necrosis factor alpha (TNF-α) further differentiates immature DCs into mature dendritic cells.

Immature DCs were incubated with vesicles prepared with HAV antigen by the method as described in Example 1. Vesicle treated immature DCs were compared to a negative control of unstimulated immature DCs and a positive control of immature DCs treated with TNF-α alone. A cytokine array assay of cell supernatant was performed using a mouse multiplex kit (Bender Medsystems). As can be seen from the results presented in Table 2, treatment of dendritic cells with vesicles of the present disclosure containing HAV antigen induces a unique cytokine profile that promotes dendritic cell differentiation.

TABLE 2

| Formulation | IL-6 (pg/ml) | TNF-α (pg/ml) | IL-1a (pg/ml) | GM-CSF (pg/ml) | IL-4 (pg/ml) |
|---|---|---|---|---|---|
| (+) control TNF-α | 34,317 | 1947 | 1891 | 124 | 12,983 |
| (−) control Unstimulated immature Dendritic Cells | 157 | 0 | 56 | 81 | 14,730 |
| Lipid Vesicles + HepA Antigen | 295 | 0 | 88 | 773 | 28,878 |

Maturation of immature DCs was also measured by flow cytometry using anti-MHC II and anti-CD86 antibodies. Mature DCs were defined as double positive for both antibodies. Maturation of immature DCs treated with vesicles prepared with HAV antigen was compared to a negative control of unstimulated DCs and a positive control treated with Lipopolysaccharide (LPS), as measured by flow cytometry using anti-MHC II and anti-CD86 antibodies.

Figure 1:
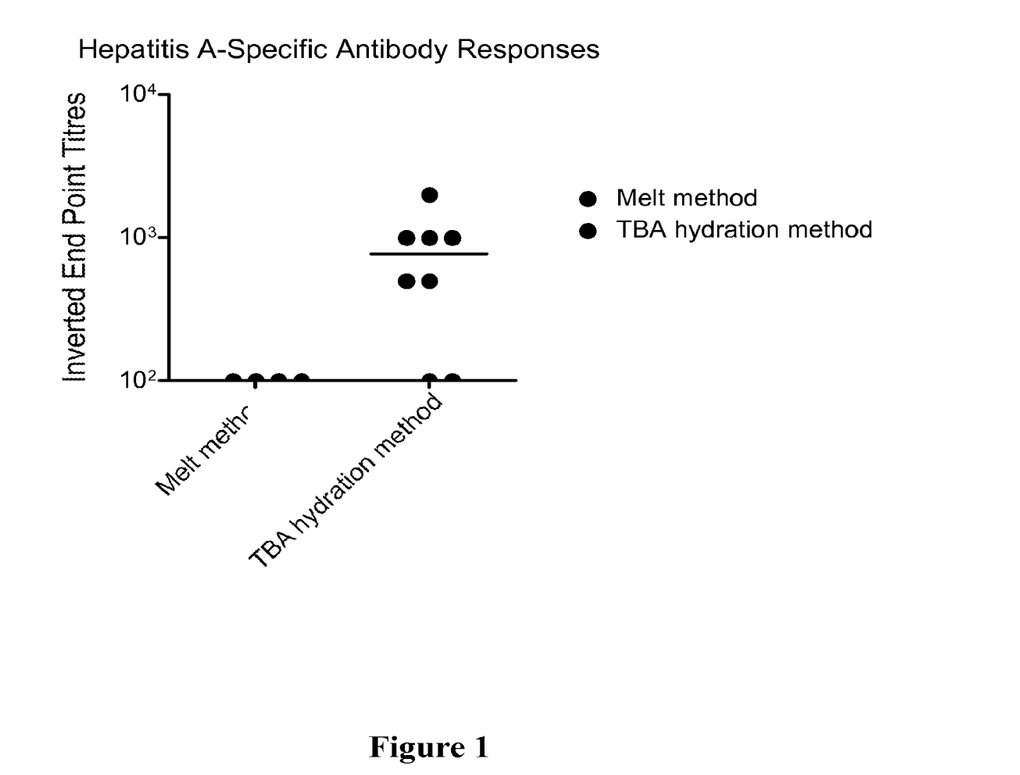
FIG. 1 is a graph which compares the immunogenicity of a Hepatitis A containing vesicle formulation prepared using a method of the present disclosure and an alternative melt-based method. Immunogenicity was evaluated in balb/c mice two weeks after three oral immunizations. Each data point represents the endpoint antibody titer measured by ELISA.
Figure 2:
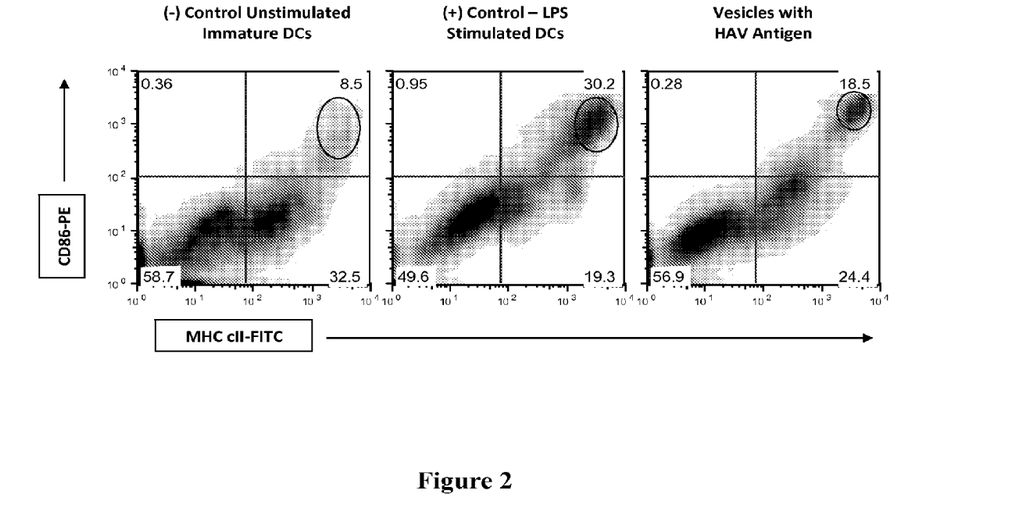
FIG. 2 shows that vesicles with Hepatitis A virus antigen that were prepared in accordance with the present disclosure induced immature dendritic cell maturation as evidenced by flow cytometry. Maturation of immature dendritic cells was measured by flow cytometry using anti-MHC II and anti-CD86 antibodies. Mature dendritic cells were defined as double positive for both antibodies. Immature dendritic cells were treated with vesicles prepared with HAV antigen and compared to a negative control of unstimulated immature dendritic cells and a positive control of immature dendritic cells treated with Lipopolysaccharide (LPS).

Mature DCs were defined as double positive for both antibodies. As shown in FIG. 2, immature DCs treated with vesicles prepared with HAV antigen promoted the maturation of immature DCs which is thought to induce a protective immune response in the intestine.

INCORPORATION BY REFERENCE

The contents of any reference that is referred to herein are hereby incorporated by reference in their entirety.

Other Embodiments

It is intended that the specification and examples be considered as exemplary only. Other embodiments will be apparent to those skilled in the art from a consideration of the specification or practice of the methods, formulations and kits disclosed herein.

In particular, while the foregoing discussion has focused on the entrapment of antigens, it is to be understood that in general, the methods may be used to entrap any substance whether antigenic or non-antigenic. Therefore, in some embodiments, the methods of the present disclosure may be used to entrap one or more polypeptides, polynucleotides or polysaccharides that may or may not be antigenic. Specific classes of substances include, but are not limited to, adjuvants, enzymes, receptors, neurotransmitters, hormones, cytokines, cell response modifiers such as growth factors and chemotactic factors, antibodies, haptens, toxins, interferons, ribozymes, anti-sense agents, plasmids, DNA, and RNA. In some embodiments the polypeptide may be an antibody or antibody fragment, e.g., a humanized antibody. Table 3 provides a non-limiting list of exemplary substances that could be entrapped using the methods of the present disclosure.

TABLE 3

| Substance | Reference Drug |
|---|---|
| interferon gamma-1b | Actimmune ® |
| alteplase | Activase ®/Cathflo ® |
| antihemophilic factor | Advate |
| human albumin | Albutein ® |
| laronidase | Aldurazyme ® |
| interferon alfa-n3 | Alferon N ® |
| human antihemophilic factor | Alphanate ® |
| virus-filtered human coagulation factor IX | AlphaNine ® SD |
| alefacept | Amevive ® |
| bivalirudin | Angiomax ® |
| darbepoetin alfa | Aranesp ™ |
| bevacizumab | Avastin ™ |
| interferon beta-1a | Avonex ® |
| coagulation factor IX | BeneFix ™ |
| interferon beta-1b | Betaseron ® |
| tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase | Ceredase ® |
| imiglucerase | Cerezyme ® |
| crotalidae polyvalent immune Fab | CroFab ™ |
| digoxin immune Fab | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |

TABLE 3-continued

| Substance | Reference Drug |
|---|---|
| human somatropin | GenoTropin ® |
| glucagon | GlucaGen ® |
| follitropin alfa | Gonal-F ® |
| antihemophilic factor | Helixate ® |
| factor XIII | Hemofil ® |
| insulin | Humalog ® |
| antihemophilic factor/von Willebrand factor complex-human | Humate-P ® |
| somatotropin | Humatrope ® |
| adalimumab | Humira ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ® |
| lutropin alfa, for injection | Luveris |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ |
| somatropin | Norditropin ®/Norditropin Nordiflex ® |
| insulin; zinc suspension | Novolin L ® |
| insulin; isophane suspension | Novolin N ® |
| insulin, regular | Novolin R ® |
| insulin | Novolin ® |
| coagulation factor VIIa | NovoSeven ® |
| somatropin | Nutropin ® |
| immunoglobulin intravenous | Octagam ® |
| pegylated-L-asparaginase | Oncaspar ® |
| abatacept | Orencia ™ |
| muromomab-CD3 | Orthoclone OKT3 ® |
| human chorionic gonadotropin | Ovidrel ® |
| pegylated interferon alfa-2a | Pegasys ® |
| pegylated interferon alfa-2b | PEG-Intron ™ |
| abarelix | Plenaxis ™ |
| epoietin alfa | Procrit ® |
| aldesleukin | Proleukin, IL-2 ® |
| somatrem | Protropin ® |
| dornase alfa | Pulmozyme ® |
| efalizumab | Raptiva ™ |
| interferon beta-1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| palivizumab | Synagis ™ |
| thyrotropin alfa | Thyrogen ® |
| tenecteplase | TNKase ™ |
| natalizumab | Tysabri ® |
| interferon alfa-n1 | Wellferon ® |
| drotrecogin alfa | Xigris ™ |
| omalizumab | Xolair ® |
| daclizumab | Zenapax ® |
| ibritumomab tiuxetan | Zevalin ™ |
| somatotropin | Zorbtive ™ (Serostim ®) |

In addition, while the methods of the present disclosure are thought to be particularly applicable to substances that are sensitive to their chemical and/or physical environment (e.g., biological substances such as microbes, polypeptides, polynucleotides, polysaccharides, etc.) it is to be understood that in some embodiments, the methods may also be used to entrap more stable substances including traditional small molecule therapeutics.

What is claimed is:

1. A method of entrapping antigens within lipid vesicles, wherein the method comprises:
   dissolving vesicle-forming lipids in tert-butanol to produce a lipid solution, wherein the lipid solution comprises 1-monopalmitoyl glycerol, dicetylphosphate, cholesterol, and a bile acid comprising sodium deoxycholate, at a ratio of 5:1:4:0.5;
   lyophilizing the lipid solution to produce a lyophilized lipid product; and
   rehydrating the lyophilized lipid product with an aqueous solution comprising an antigen consisting of an attenuated or inactivated virus such that antigen-containing lipid vesicles are formed.

2. The method of claim 1, wherein the aqueous antigen solution further comprises a lyoprotectant.

3. The method of claim 2, wherein the lyoprotectant is sucrose.

4. The method of claim 1, wherein the attenuated virus or inactivated virus is hepatitis A or influenza.

5. The method of claim 1, further comprising a step of adding an adjuvant after the antigen-containing lipid vesicles are formed.

6. The method of claim 1, wherein the lyophilized lipid product comprises an adjuvant.

7. The method of claim 1, further comprising a step of lyophilizing the antigen-containing lipid vesicles.

8. The method of claim 7, further comprising a step of rehydrating the antigen-containing lipid vesicles after they have been lyophilized.

9. The method of claim 1, wherein the antigen exhibits reduced antigenic integrity upon exposure to tert-butanol.

* * * * *